(12) United States Patent
Chun et al.

(10) Patent No.: US 9,850,524 B2
(45) Date of Patent: Dec. 26, 2017

(54) DETECTION OF TARGET NUCLEIC ACID SEQUENCES BY PO CLEAVAGE AND HYBRIDIZATION

(75) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 188 days.

(21) Appl. No.: 14/114,253

(22) PCT Filed: May 3, 2012

(86) PCT No.: PCT/KR2012/003497
§ 371 (c)(1),
(2), (4) Date: Oct. 28, 2013

(87) PCT Pub. No.: WO2012/150835
PCT Pub. Date: Nov. 8, 2012

(65) Prior Publication Data
US 2014/0073534 A1    Mar. 13, 2014

(30) Foreign Application Priority Data

| May 4, 2011 | (KR) | 10-2011-0042332 |
| Jul. 12, 2011 | (KR) | 10-2011-0068888 |
| Dec. 2, 2011 | (WO) | PCT/KR2011/009317 |

(51) Int. Cl.
*C12Q 1/68* (2006.01)
*C12Q 1/34* (2006.01)

(52) U.S. Cl.
CPC .................................. *C12Q 1/6823* (2013.01)

(58) Field of Classification Search
None
See application file for complete search history.

(56) References Cited

U.S. PATENT DOCUMENTS

| 5,210,015 A | 5/1993 | Gelfand et al. |
| 5,538,848 A | 7/1996 | Livak et al. |
| (Continued) | | |

FOREIGN PATENT DOCUMENTS

| EP | 1564306 A2 | 8/2005 |
| EP | 1777298 A1 | 4/2007 |
| (Continued) | | |

OTHER PUBLICATIONS

"Viruses" (Wikipedia.com, accessed Nov. 24, 2012).*
(Continued)

*Primary Examiner* — Joseph G. Dauner
(74) *Attorney, Agent, or Firm* — Gianna Julian-Arnold; Saul Ewing Arnstein & Lehr LLP

(57) ABSTRACT

The present invention relates to the detection of a target nucleic acid sequence by a POCH (PO Cleavage and Hybridization) assay on a solid substrate. The present invention detects the target nucleic acid sequence by use of in which the PO (Probing Oligonucleotide) hybridized with the target nucleic acid sequence is cleaved and the cleavage of the PO is detected by hybridization with the CO (Capturing Oligonucleotide). In the present invention, an uncleaved PO is hybridized with the CO immobilized onto the solid substrate. The designs of the PO and the CO are convenient and the optimization of reaction conditions is routinely easy in the present invention. Where the detection of signal on the solid substrate is continuously performed along with repetition of cleavage of the POs in the present invention, the number of the POs cleaved is increased upon the repetition number of the cleavage reaction and the signal is changed in parallel with the number of the POs cleaved. Then, the target nucleic acid sequence can be detected in a real-time manner. In contrast, the change of the signal is not observed in the absence of the target nucleic acid sequence.

34 Claims, 24 Drawing Sheets

(56) References Cited

U.S. PATENT DOCUMENTS

| | | |
|---|---|---|
| 5,691,142 A | 11/1997 | Dahlberg et al. |
| 6,326,145 B1 | 12/2001 | Whitcombe et al. |
| 6,893,819 B1 | 5/2005 | Sorge |
| 7,381,532 B2 | 6/2008 | Sorge |
| 2002/0045738 A1 | 4/2002 | Singh et al. |
| 2004/0191823 A1 | 9/2004 | Virgos et al. |
| 2005/0142595 A1 | 6/2005 | Maletta et al. |
| 2005/0221315 A1 | 10/2005 | Braven et al. |
| 2006/0110748 A1 | 5/2006 | Sorge |
| 2006/0246469 A1 | 11/2006 | Sorge |
| 2007/0099211 A1 | 5/2007 | Aivazachvili et al. |
| 2007/0231815 A1 | 10/2007 | Sorge |
| 2008/0131890 A1 | 6/2008 | Allawi et al. |
| 2008/0160535 A1 | 7/2008 | Gold et al. |
| 2008/0193940 A1 | 8/2008 | Aivazachvili et al. |
| 2008/0241838 A1 | 10/2008 | Scaboo et al. |
| 2009/0305237 A1 | 12/2009 | Cantor et al. |
| 2010/0041049 A1 | 2/2010 | Smith et al. |
| 2011/0281266 A1 | 11/2011 | Sergeev et al. |

FOREIGN PATENT DOCUMENTS

| | | |
|---|---|---|
| EP | 2060637 A1 | 5/2009 |
| EP | 2256216 A1 | 1/2010 |
| JP | 2003334097 | 11/2003 |
| JP | 2004305219 A | 11/2004 |
| KR | 1020090067334 A | 6/2009 |
| WO | 1998023774 | 6/1998 |
| WO | 200063437 A2 | 4/2000 |
| WO | 2005010199 A2 | 2/2005 |
| WO | 2005059548 A1 | 6/2005 |
| WO | 2006004949 A1 | 1/2006 |
| WO | 2006005081 A2 | 1/2006 |
| WO | 2008076948 A1 | 6/2008 |
| WO | 2008094902 A2 | 8/2008 |
| WO | 2008102057 A1 | 8/2008 |
| WO | 2009117327 A2 | 10/2009 |
| WO | 2010055134 A1 | 5/2010 |
| WO | 2010128041 A1 | 11/2010 |
| WO | 2011028041 A2 | 3/2011 |
| WO | 2011078441 A1 | 6/2011 |
| WO | 2012096523 A2 | 7/2012 |
| WO | 2012134195 A2 | 10/2012 |
| WO | 2013115442 A1 | 8/2013 |

OTHER PUBLICATIONS

"How many species of bacteria are there" (wisegeek.com; accessed Jan. 21, 2014).*

"Fungi," (Wikipedia.com; accessed Jun. 3, 2013).*

"Plant," (Wikipedia.com; accessed Aug. 28, 2015).*

"Mammal," (Wikipedia.com; accessed Sep. 22, 2011).*

"Murinae," (Wikipedia.com, accessed Mar. 18, 2013).*

"Fish," (Wikipedia.com, accessed Nov. 2, 2014).*

"List of sequenced bacterial genomes" (Wikipedia.com; accessed Jan. 24, 2014).*

Lyamichev, V., et al.; Polymorphism identification and quantitative detection of genomic DNA by invasive cleavage of bligonucleotide probes; 1999 Nature America Inc., Nature Biotechnology, vol. 17, Mar. 1999, pp. 292-296.

Olivier, M.; The Invader® assay of SNP genotyping; Elsevier, Mutation Research, vol. 573, 2005, pp. 103-110.

Roux, P., et al.; Direct Measurement of Multiple mRNAs in Nerve Growth Factor-Induced PC12 Cells Using Electrophoretic Tags to Monitor Biomarkers of Neuronal Differentiation in 96-Well Format; ASSAY and Drug Development Technologies, vol. 2, No. 6, 2004, pp. 637-646.

Allawi, H., et al.; Quantitation of microRNAs using a modified Invader assay; RNA Society, vol. 10, 2004, pp. 1153-1161.

Yuan, Y., et al.; Establishment of a Modified High Resolution Melting Assay Based on Allele-specific-extension to Determine Single Nucleotide Polymorphism; Journal of Capital Medical University, vol. 31, No. 6, Dec. 2010, pp. 742-747 [Abstract].

Lohmann et al. A new enzymatic route for production of long 5'-phosphorylated oligonucleotides using suicide cassettes and rolling circle DNA synthesis. BMC Biotechnology. 2007, vol. 7, No. 49.

Hessner et al. Genotyping of Factor V G1691A (Leiden) without the Use of PCR by Invasive Cleavage of Oligonucleotide Probes. Clinical Chemistry. vol. 46, No. 8, pp. 1051-1056.

Lambda Exonuclease from thermofisher.com/order/catalog/product/EN0561 (U.S. Appl. No. 14/008,096).

Nurmi, et al., A new label technology for the detection of specific polymerase chain reaction products in a closed tube. Nucleic Acids Research, 28, e280, 2000 (U.S. Appl. No. 14/008,096).

* cited by examiner

PROBING OLIGONUCLEOTIDE (PO)
A. NON-TAGGED PO
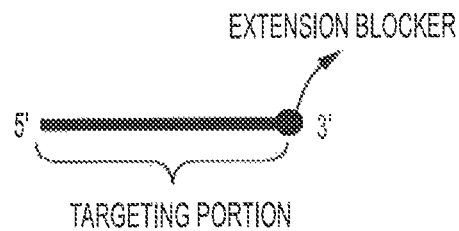
B. 3'-TAGGED PO
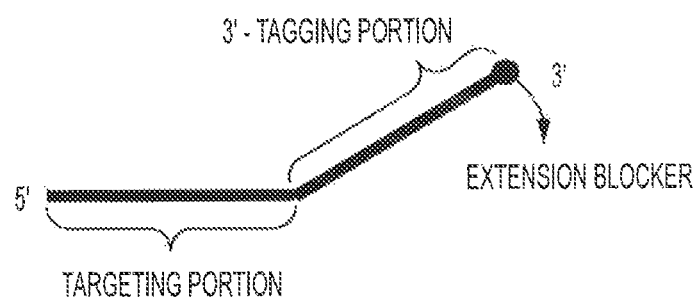
C. 5'-TAGGED PO
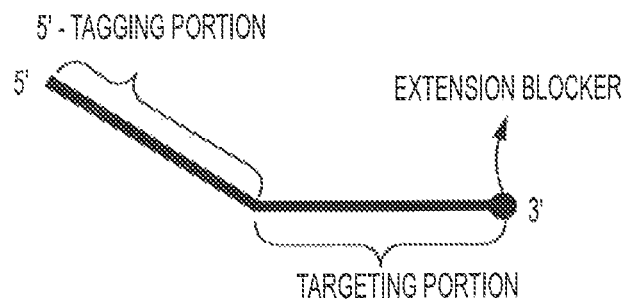
FIG. 1A CAPTURING OLIGONUCLEOTIDE (CO) ON SOLID SUPPORT
A. IMMOBILIZATION OF CO THROUGH ITS 3'-END
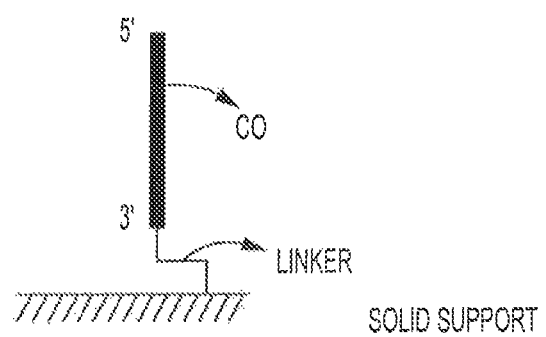
B. IMMOBILIZATION OF CO THROUGH ITS 5'-END
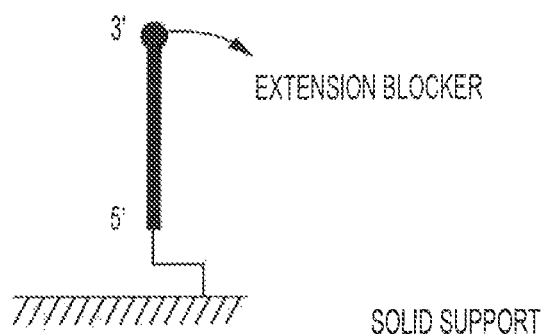
FIG. 1B A. HYBRIDIZATION
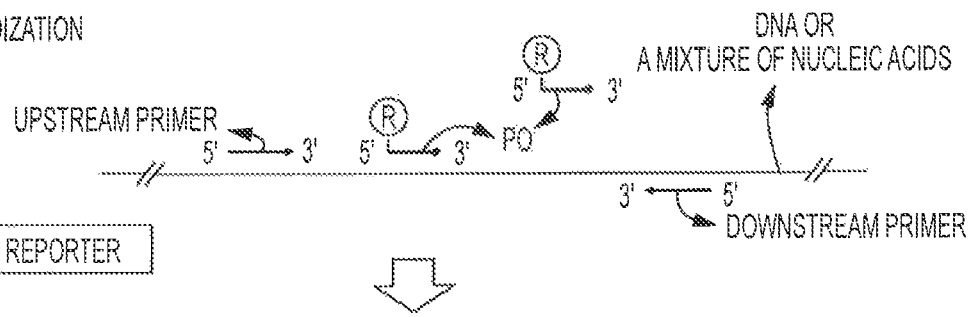
R : REPORTER
B. PRIMER EXTENSION & CLEAVAGE OF PO
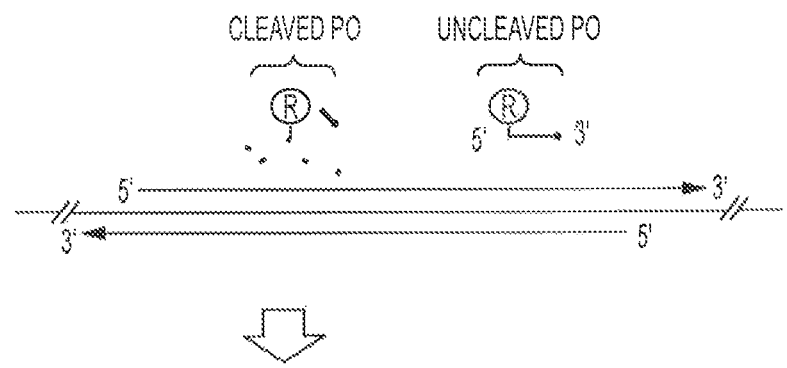
C. HYBRIDIZATION OF PO TO CO & DETECTION
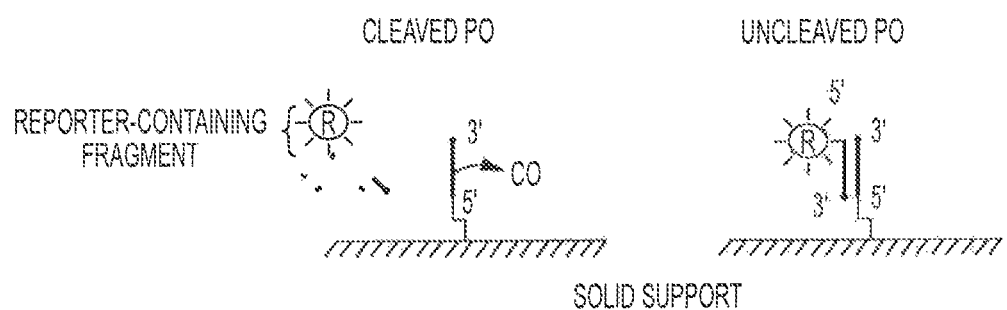
SOLID SUPPORT
FIG. 2

A. HYBRIDIZATION
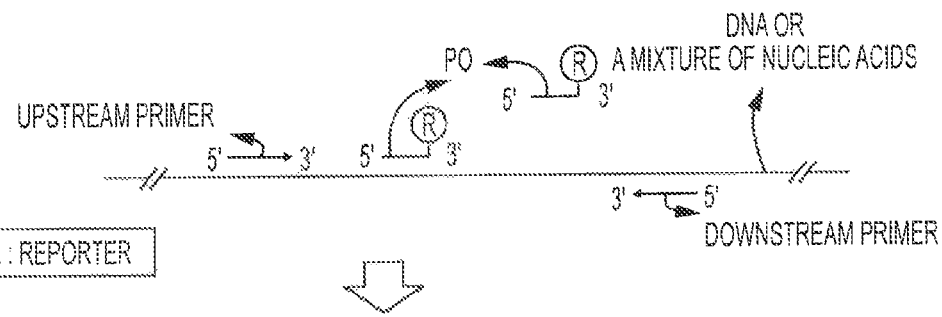
B. PRIMER EXTENSION & CLEAVAGE OF PO
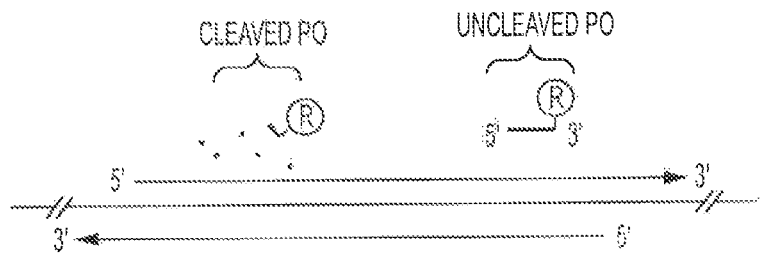
C. HYBRIDIZATION OF PO TO CO & DETECTION
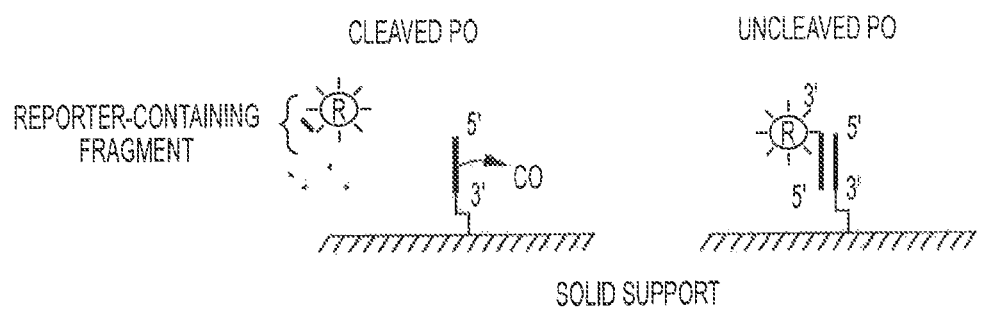
FIG. 3

A. HYBRIDIZATION
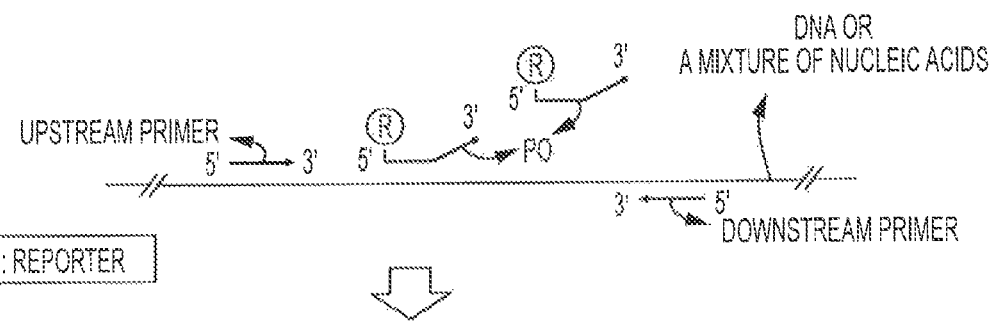
B. PRIMER EXTENSION & CLEAVAGE OF PO
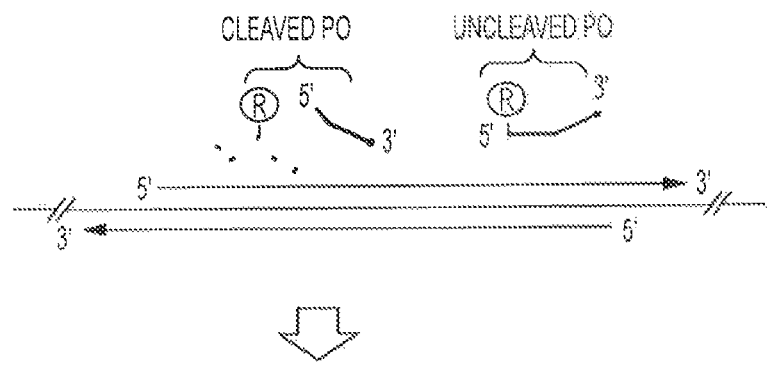
C. HYBRIDIZATION OF PO TO CO & DETECTION
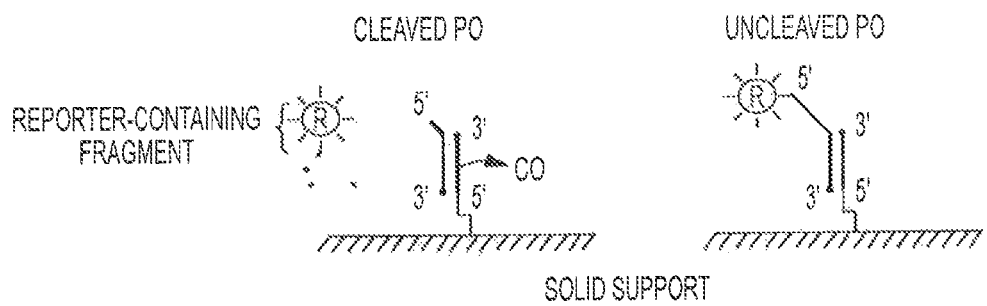
FIG. 4

A. HYBRIDIZATION
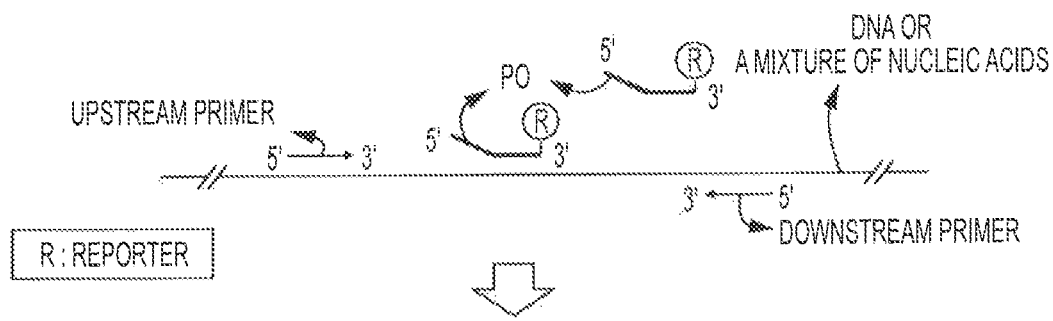
B. PRIMER EXTENSION & CLEAVAGE OF PO
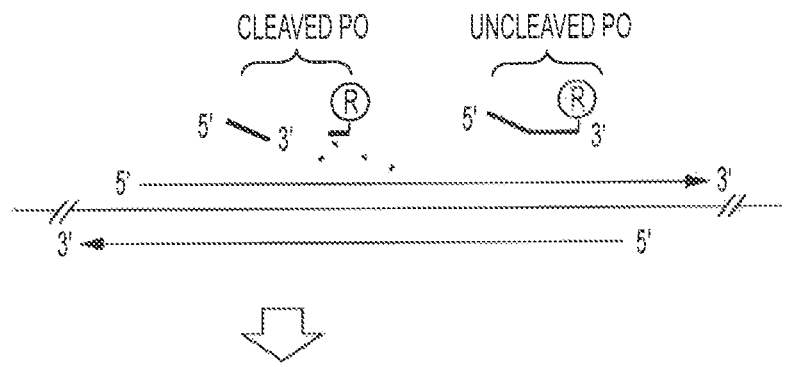
C. HYBRIDIZATION OF PO TO CO & DETECTION
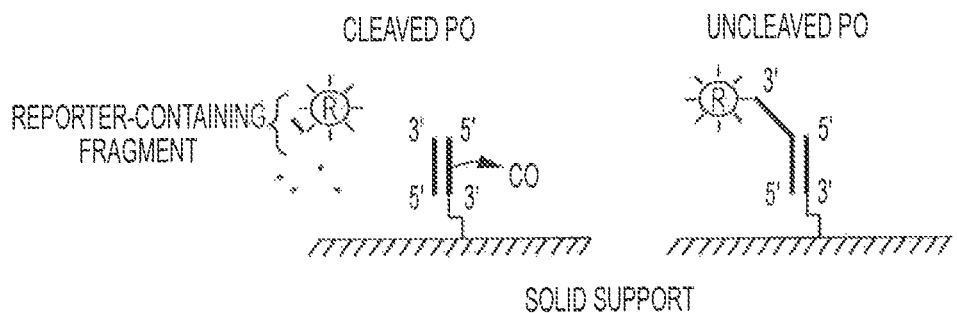
FIG. 5

A. HYBRIDIZATION
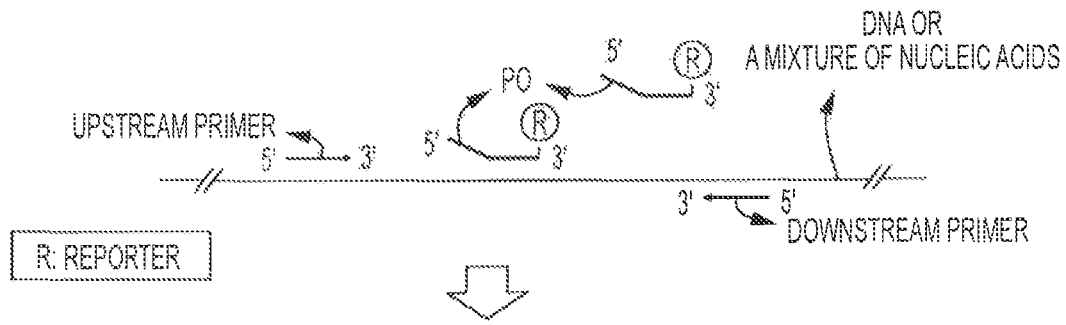
B. PRIMER EXTENSION & CLEAVAGE OF PO
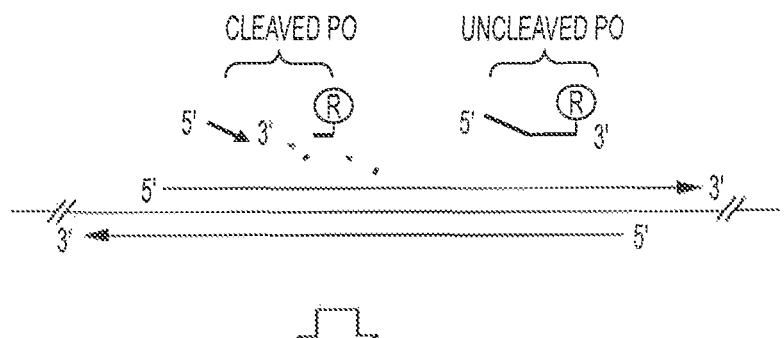
C. HYBRIDIZATION OF PO TO CO & DETECTION
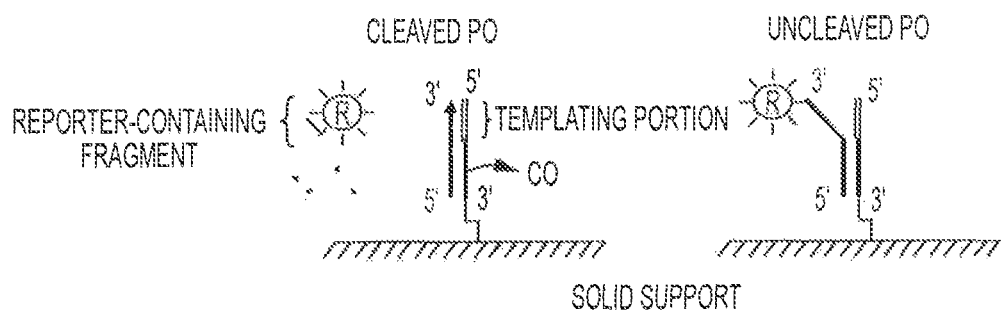
FIG. 6

A. HYBRIDIZATION
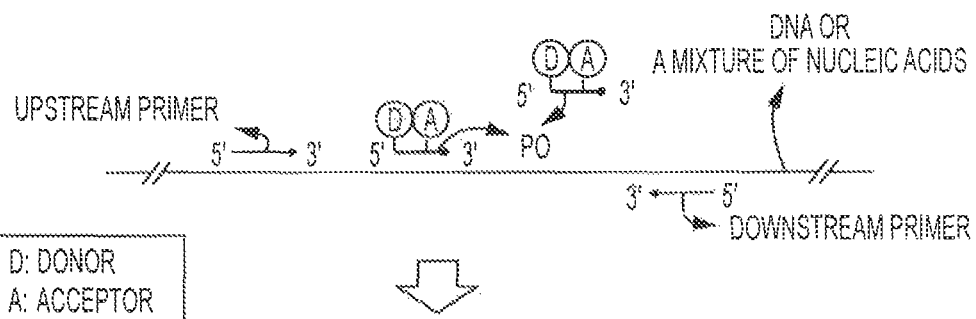
B. PRIMER EXTENSION & CLEAVAGE OF PO
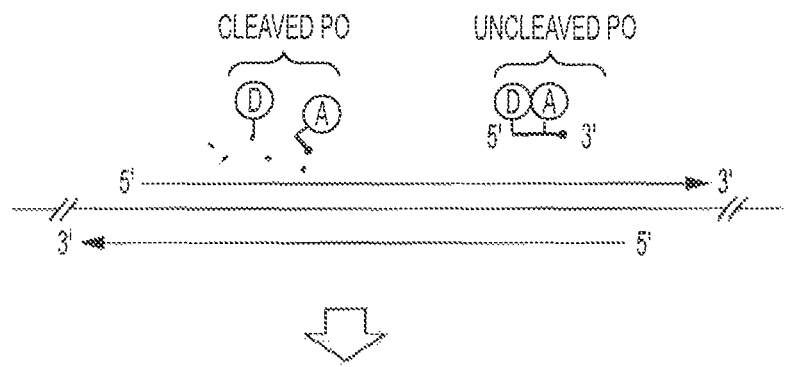
C. HYBRIDIZATION OF PO TO CO & DETECTION
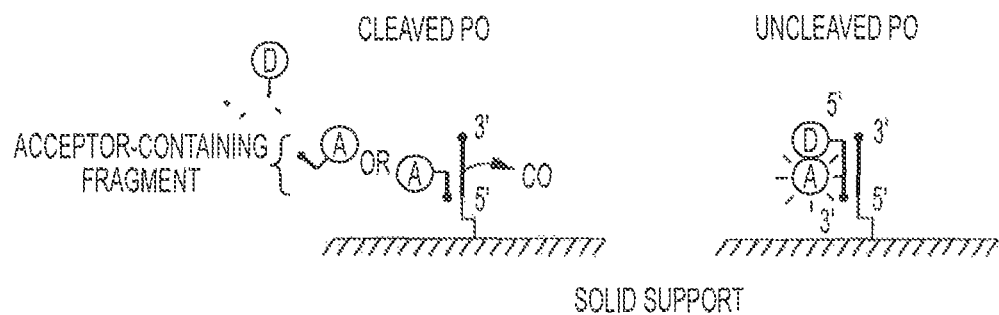
FIG. 7

A. HYBRIDIZATION
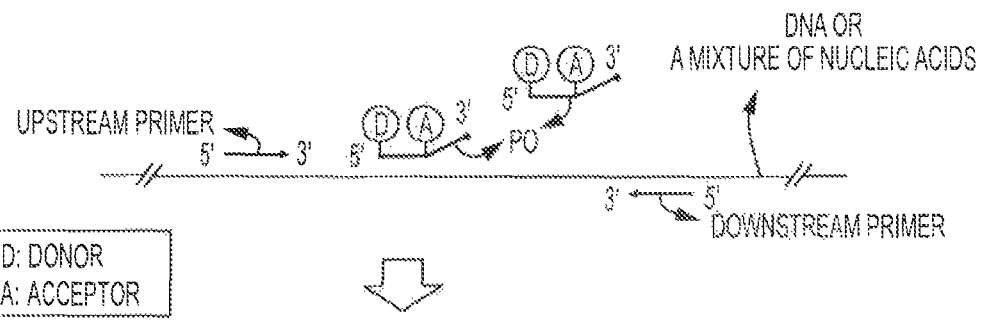
D: DONOR
A: ACCEPTOR
B. PRIMER EXTENSION & CLEAVAGE OF PO
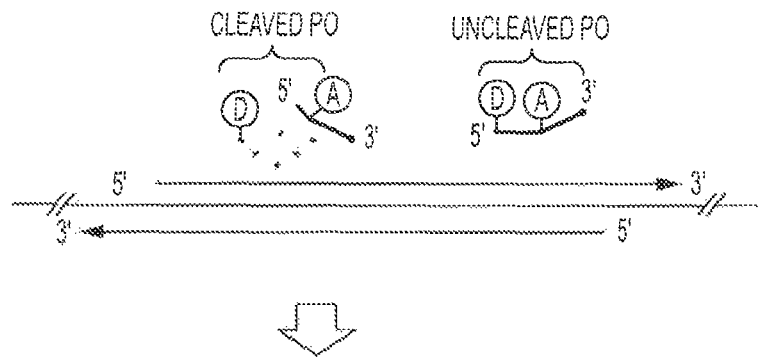
C. HYBRIDIZATION OF PO TO CO & DETECTION
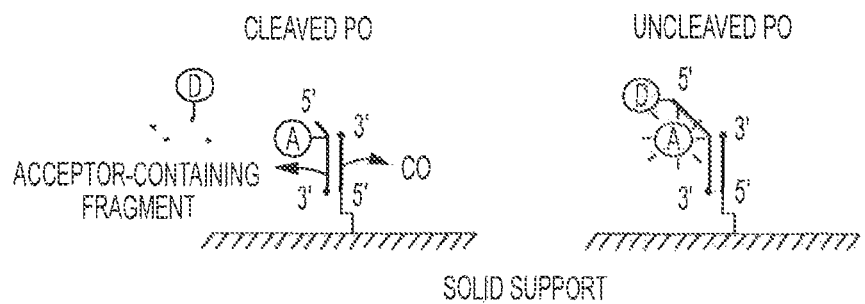
FIG. 8

A. HYBRIDIZATION
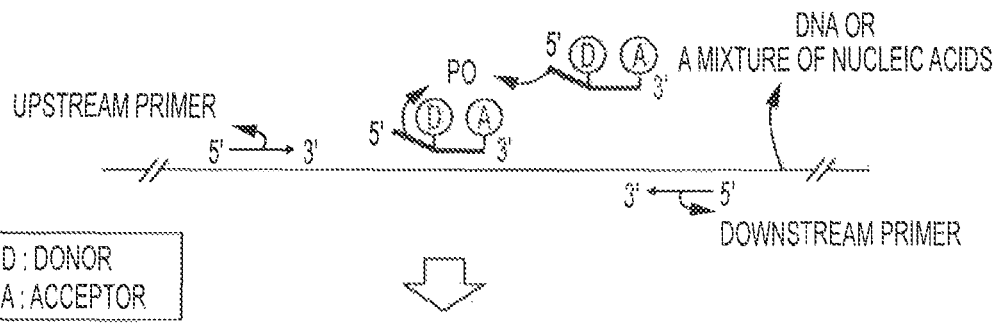
D : DONOR
A : ACCEPTOR
B. PRIMER EXTENSION & CLEAVAGE OF PO
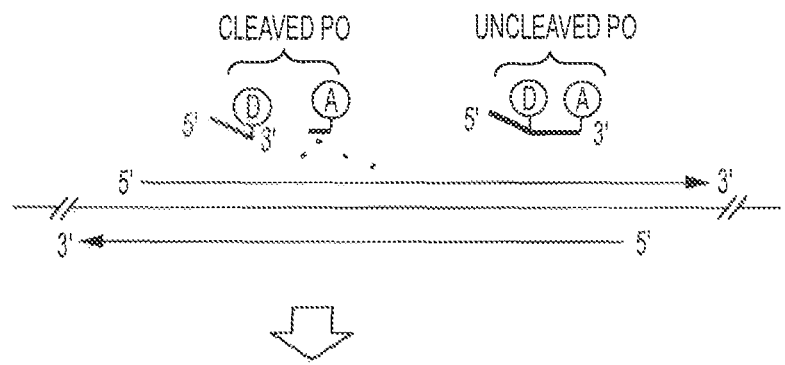
C. HYBRIDIZATION OF PO TO CO & DETECTION
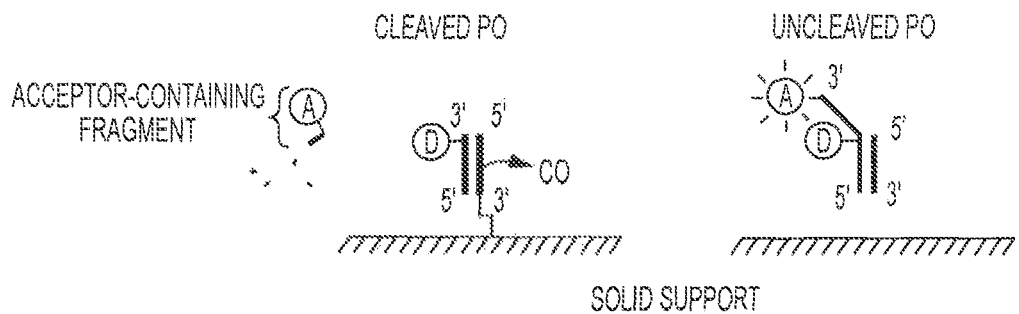
SOLID SUPPORT
FIG. 9

A. HYBRIDIZATION
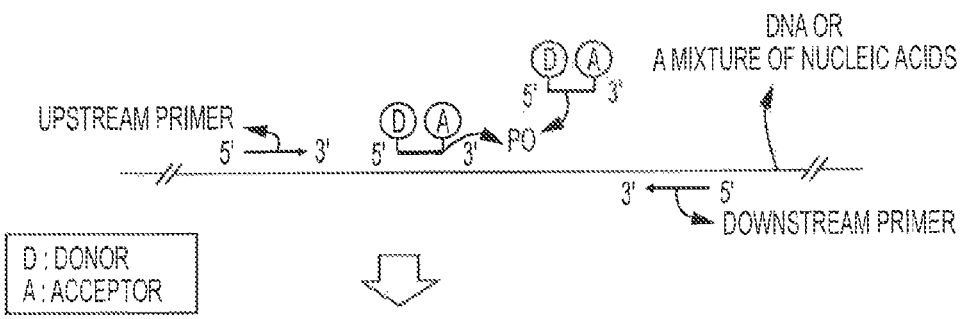
B. PRIMER EXTENSION & CLEAVAGE OF PO
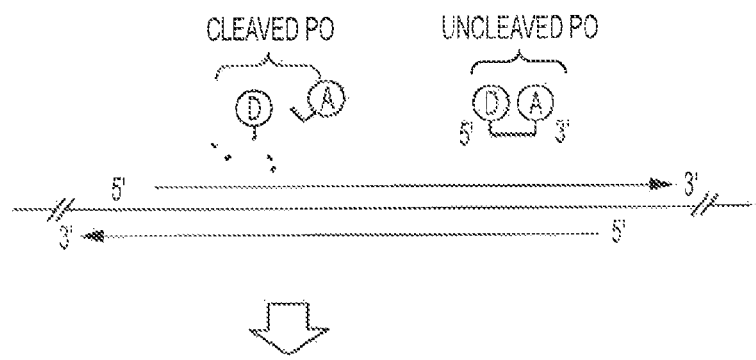
C. HYBRIDIZATION OF PO TO CO & DETECTION
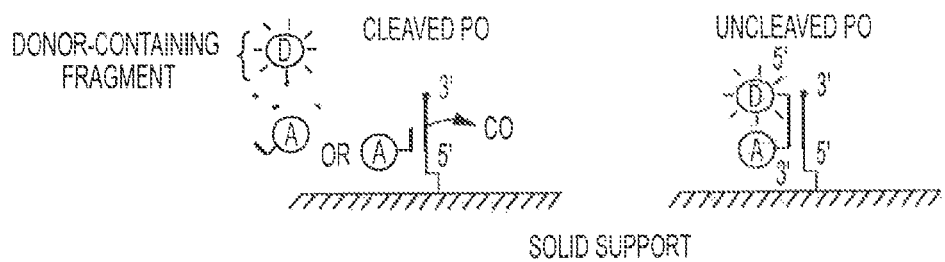
FIG. 10

A. HYBRIDIZATION
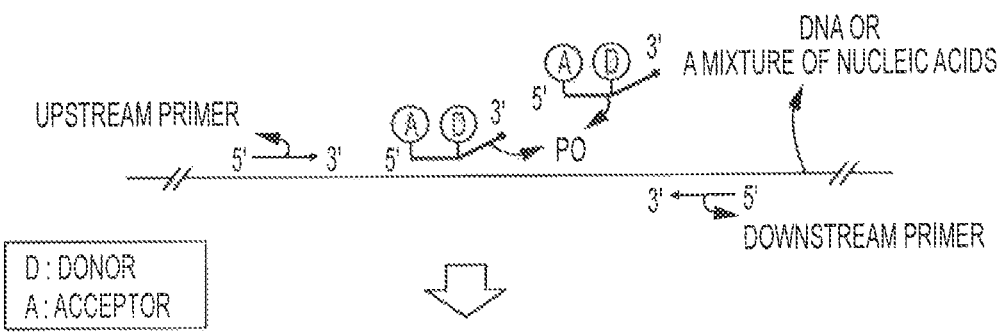
B. PRIMER EXTENSION & CLEAVAGE OF PO
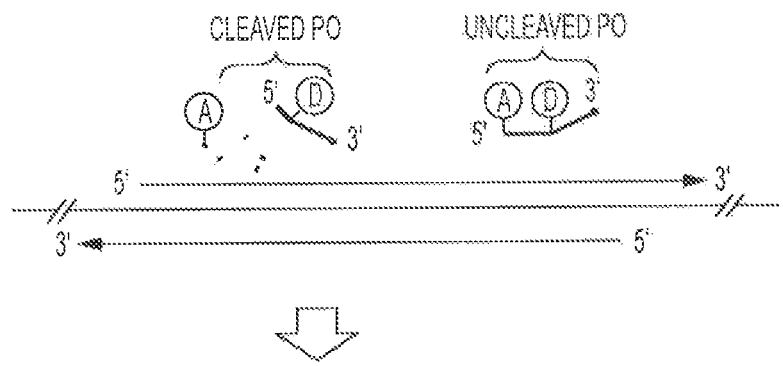
C. HYBRIDIZATION OF PO TO CO & DETECTION
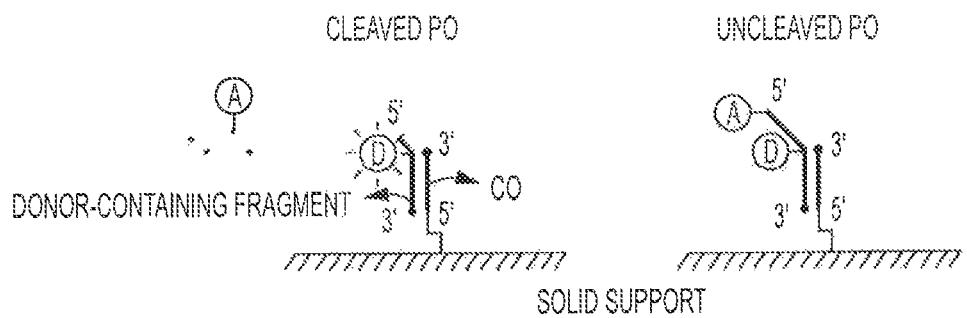
FIG. 11

A. HYBRIDIZATION
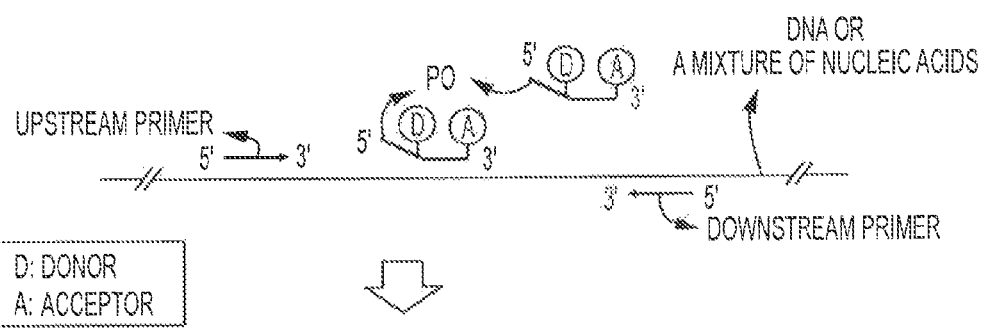
D: DONOR
A: ACCEPTOR
B. PRIMER EXTENSION & CLEAVAGE OF PO
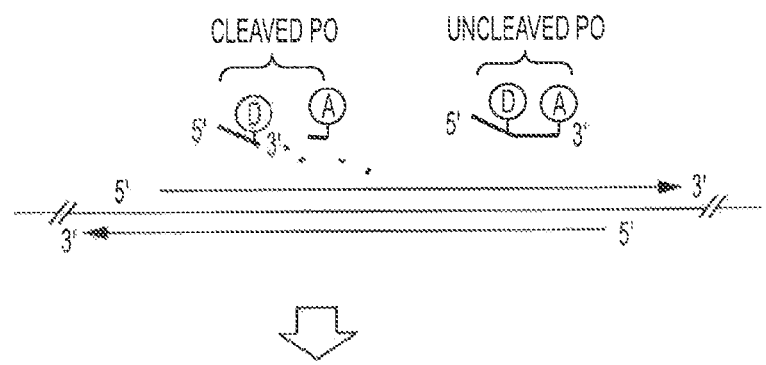
C. HYBRIDIZATION OF PO TO CO & DETECTION
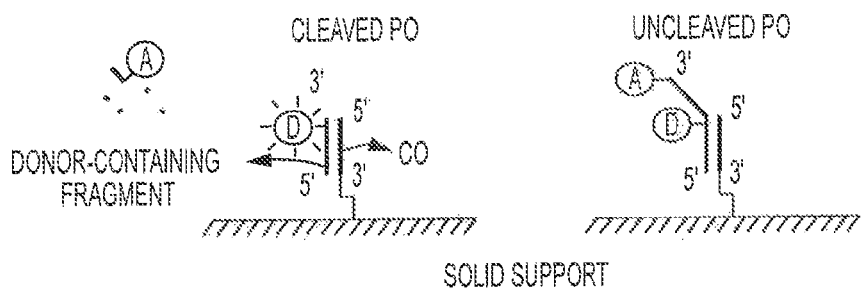
FIG. 12

A. HYBRIDIZATION
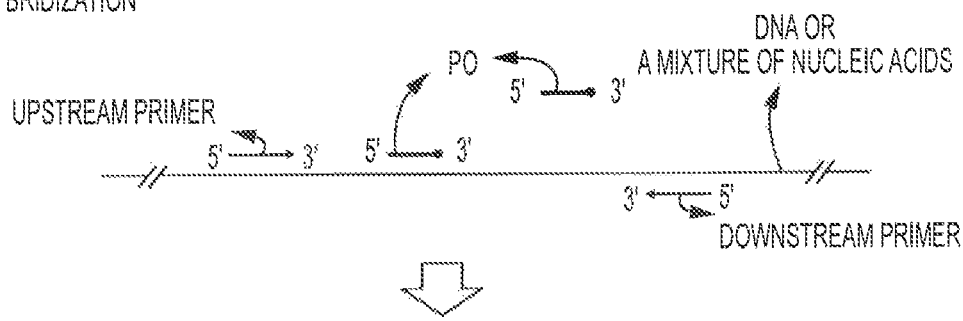
B. PRIMER EXTENSION & CLEAVAGE OF PO
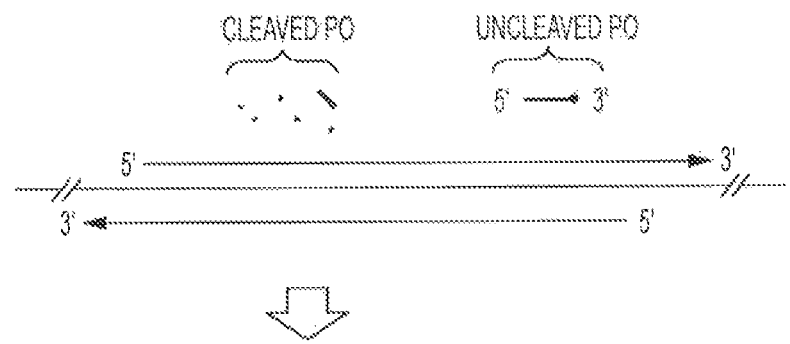
C. HYBRIDIZATION OF PO TO CO & DETECTION
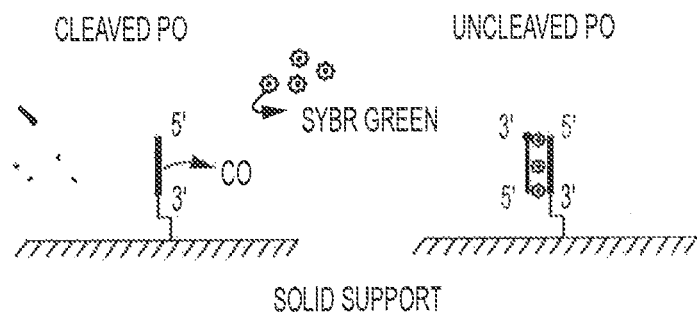
FIG. 13

POCH ASSAY WITH A SINGLE-LABELED NON-TAGGED PO

A. FLUORESCENT IMAGE ON MICROARRAY

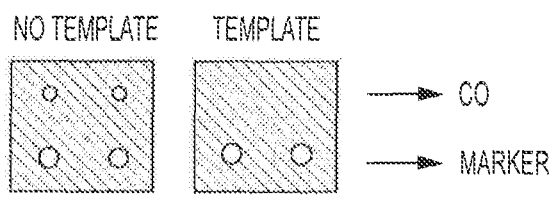

B. FLUORESCENT INTENSITY ON MICROARRAY

| TEMPLATE [1] | UPSTREAM PRIMER | NON-TAGGED PO [2] | CO [3] | RFU [4] |
|---|---|---|---|---|
| − | + | + | + | 65,484 (±0.7) |
| + | + | + | + | 9,006 (±20.5) |

1) TEMPLATE IS A SYNTHETIC OLIGONUCLEOTIDE FOR *NEISSERIA GONORRHOEAE* GENE.

2) NON-TAGGED PO HAS A FLUORESCENT REPORTER MOLECULE AT ITS 5'-END.

3) CO IS MODIFIED BY C3 SPACER AT ITS 3'-END AND IMMOBILIZED ON THE SURFACE OF SOLID SUBSTRATE BY USING AN AMINO GROUP AT ITS 5'-END.

4) RFU REPRESENTS RELATIVE FLUORESCENCE UNITS.

FIG. 14

POCH ASSAY WITH A SINGLE-LABELED 3'-TAGGED PO

A. FLUORESCENT IMAGE ON MICROARRAY

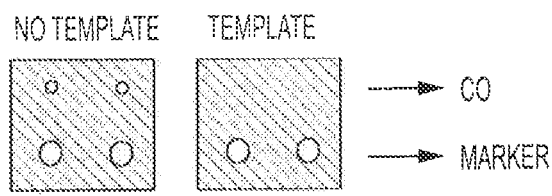

B. FLUORESCENT INTENSITY ON MICROARRAY

| TEMPLATE 1) | UPSTREAM PRIMER | 3'-TAGGED PO 2) | CO 3) | RFU 4) |
|---|---|---|---|---|
| - | + | + | + | 65,464 (±6.4) |
| + | + | + | + | 10,217 (±73.5) |

1) TEMPLATE IS A SYNTHETIC OLIGONUCLEOTIDE FOR *NEISSERIA GONORRHOEAE* GENE.

2) A 3'-TAGGED PO HAS A FLUORESCENT REPORTER MOLECULE AT ITS 5'-END.

3) CO IS MODIFIED BY C3 SPACER AT ITS 3'-END AND IMMOBILIZED ON THE SURFACE OF SOLID SUBSTRATE BY USING AN AMINO GROUP AT ITS 5'-END. THE CO COMPRISES A NUCLEOTIDE SEQUENCE HYBRIDIZABLE WITH THE 3'-TAGGING PORTION OF THE PO.

4) RFU REPRESENTS RELATIVE FLUORESCENCE UNITS.

FIG. 15

POCH ASSAY WITH A SINGLE-LABELED 5'-TAGGED PO

A. FLUORESCENT IMAGE ON MICROARRAY

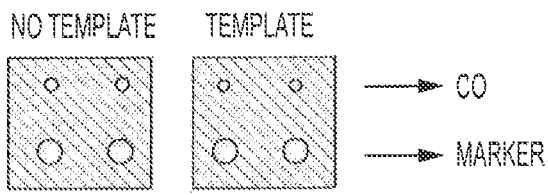

B. FLUORESCENT INTENSITY ON MICROARRAY

| TEMPLATE 1) | UPSTREAM PRIMER | 5'-TAGGED PO 2) | CO 3) | RFU 4) |
|---|---|---|---|---|
| − | + | + | + | 65,455 (±0.7) |
| + | + | + | + | 17,586 (±152.0) |

1) TEMPLATE IS A SYNTHETIC OLIGONUCLEOTIDE FOR *NEISSERIA GONORRHOEAE* GENE.

2) A 5'-TAGGED PO HAS A FLUORESCENT REPORTER MOLECULE AT ITS 3'-END.

3) CO IS IMMOBILIZED ON THE SURFACE OF SOLID SUBSTRATE BY USING AN AMINO GROUP AT ITS 3'-END. THE CO COMPRISES A NUCLEOTIDE SEQUENCE HYBRIDIZABLE WITH THE 5'-TAGGING PORTION OF THE PO.

4) RFU REPRESENTS RELATIVE FLUORESCENCE UNITS.

FIG. 16

POCH ASSAY WITH A DUAL-LABELED 3'-TAGGED PO

A. FLUORESCENT IMAGE ON MICROARRAY

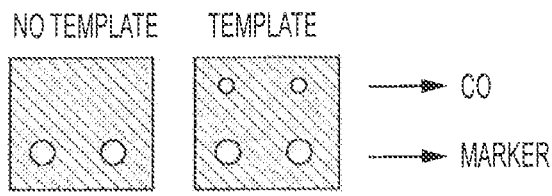

B. FLUORESCENT INTENSITY ON MICROARRAY

| TEMPLATE 1) | UPSTREAM PRIMER | 3'-TAGGED PO 2) | CO 3) | RFU 4) |
|---|---|---|---|---|
| – | + | + | + | 13,349 (±441.2) |
| + | + | + | + | 65,469 (±0.7) |

1) TEMPLATE IS A SYNTHETIC OLIGONUCLEOTIDE FOR *NEISSERIA GONORRHOEAE* GENE.

2) A 3'-TAGGED PO HAS A ACCEPTOR MOLECULE AT ITS 5'-END AND A DONOR MOLECULE AT ITS 3'-PORTION.

3) CO IS MODIFIED BY C3 SPACER AT ITS 3'-END AND IMMOBILIZED ON THE SURFACE OF SOLID SUBSTRATE BY USING AN AMINO GROUP AT ITS 5'-END. THE CO COMPRISES A NUCLEOTIDE SEQUENCE HYBRIDIZABLE WITH THE 3'-TAGGING PORTION OF THE PO.

4) RFU REPRESENTS RELATIVE FLUORESCENCE UNITS.

FIG. 17

POCH ASSAY WITH A SINGLE-LABELED NON-TAGGED PO

A. FLUORESCENT IMAGE ON MICROARRAY

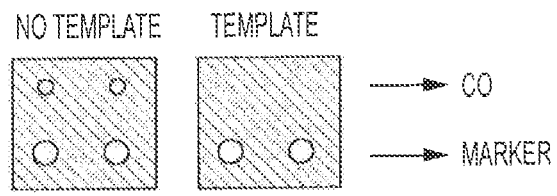

B. FLUORESCENT INTENSITY ON MICROARRAY

| TEMPLATE 1) | PRIMERS 2) | NO-TAGGED PO 3) | CO 4) | RFU 5) |
|---|---|---|---|---|
| – | + | + | + | 65,474 (±0.0) |
| + | + | + | + | 1,650 (±97.6) |

1) TEMPLATE IS A GENOMIC DNA OF *NEISSERIA GONORRHOEAE*.

2) PRIMERS ARE AN UPSTREAM AND A DOWNSTREAM PRIMER FOR PCR.

3) NON-TAGGED PO HAS A FLUORESCENT REPORTER MOLECULE AT ITS 5'-END.

4) CO IS MODIFIED BY C3 SPACER AT ITS 3'-END AND IMMOBILIZED ON THE SURFACE OF SOLID SUBSTRATE BY USING AN AMINO GROUP AT ITS 5'-END.

5) RFU REPRESENTS RELATIVE FLUORESCENCE UNITS.

FIG. 18

POCH ASSAY WITH A SINGLE-LABELED 3'-TAGGED PO

A. FLUORESCENT IMAGE ON MICROARRAY

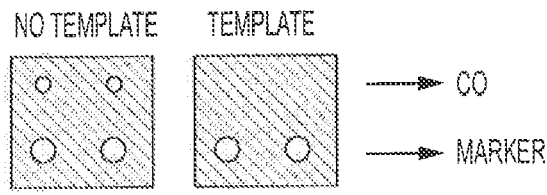

B. FLUORESCENT INTENSITY ON MICROARRAY

| TEMPLATE [1] | PRIMERS [2] | 3'-TAGGED PO [3] | CO [4] | RFU [5] |
|---|---|---|---|---|
| − | + | + | + | 65,470 (±1.4) |
| + | + | + | + | 9,969 (±217.1) |

1) TEMPLATE IS A GENOMIC DNA OF *NEISSERIA GONORRHOEAE*.

2) PRIMERS ARE AN UPSTREAM AND A DOWNSTREAM PRIMER FOR PCR.

3) A 3'-TAGGED PO HAS A FLUORESCENT REPORTER MOLECULE AT ITS 5'-END.

4) CO IS MODIFIED BY C3 SPACER AT ITS 3'-END AND IMMOBILIZED ON THE SURFACE OF SOLID SUBSTRATE BY USING AN AMINO GROUP AT ITS 5'-END. THE CO COMPRISES A NUCLEOTIDE SEQUENCE HYBRIDIZABLE WITH THE 3'-TAGGING PORTION OF THE PO.

5) RFU REPRESENTS RELATIVE FLUORESCENCE UNITS.

FIG. 19

DETECTION OF TARGET NUCLEIC ACID SEQUENCES BY PO CLEAVAGE AND HYBRIDIZATION

CROSS REFERENCE TO RELATED APPLICATIONS

This application claims the priority of PCT/KR2012/003497, filed on May 3, 2012, and PCT/KR2011/009317, filed on Dec. 2, 2011, which claim the benefit of priority to Korean Application Nos. 10-2011-0068888, filed on Jul. 12, 2011, and 10-2011-0042332, filed on May 4, 2011, the entire contents of each of which are hereby incorporated in total by reference.

SEQUENCE LISTING

This application incorporates by reference the Sequence Listing contained in an ASCII text file named "361406-00018_SeqList" submitted via EFS-Web. The text file was created on Oct. 24, 2013, and is 3.27 kb in size.

BACKGROUND OF THE INVENTION

Field of the Invention

The present invention relates to the detection of a target nucleic acid sequence by a POCH (PO Cleavage and Hybridization) assay on a solid substrate.

Description of the Related Art

DNA hybridization-based technologies would be a very useful tool in specific nucleic acid sequence determination and clearly be valuable in clinical diagnosis, genetic research, and forensic laboratory analysis. Besides probe hybridization processes, several approaches using additional enzymatic reactions, for example, TaqMan™ probe method, have been suggested.

In TaqMan™ probe method, the labeled probe hybridized with target nucleic acid sequences is cleaved by a 5' nuclease activity of an upstream primer-dependent DNA polymerase and a labeled fragment is released (U.S. Pat. Nos. 5,210,015, 5,538,848 and 6,326,145). The release of the labeled fragment indicates cleavage of the probe, finally indicating the presence of target sequences. The detection of the labeled fragment may be performed by size analysis such as gel electrophoresis, sedimentation in gradients, gel exclusion chromatography and homochromatography. The cleavage of probes may be carried out in a real-time manner by use of interactive dual labels.

The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with target sequences is also cleaved to form a fragment comprising the 5'-tail region.

There have been reported some methods in which probes having a 5'-tail region non-complementary to target sequences are cleaved by 5' nuclease to release a fragment comprising the 5'-tail region and target detection is performed using the fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect target sequences.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label.

U.S. Pat. Appln. Pub. 2008-0241838 discloses a target detection method using cleavage of single-labeled probes having non-complementary 5' portion to target and capture probes immobilized on solid substrates. A single label is positioned on the non-complementary 5' portion of the labeled probe. The labeled probes hybridized with target are cleaved to release fragments, after which the fragments are then hybridized with the capture probes to detect the presence of the target sequence. In this method, it is necessary that an uncleaved/intact probe is not hybridized with the capture probe. For this performance, the method prevents the uncleaved target probe from hybridizing with the immobilized capture-probe by controlling immobilization orientation of the immobilized oligonucleotide and its distance from the surface of a solid substrate. However, such limitation results in lower efficiency of hybridization on a solid substrate and difficulties in optimization of reaction conditions.

U.S. Pat. Appln. Pub. 2008-0193940 also discloses a target detection method using probes having non-complementary sequence (tag or flap sequence) to target as well as capture probes immobilized on solid substrates. A label is also positioned on the non-complementary region of probes. Undigested probes form hairpin structure and is not hybridized with capture probes. In contrast, where probes are digested, label-containing fragments are then hybridized with capture probes, thereby detecting the presence of target nucleic acid sequences. However, it has serious problems in which reaction conditions has to be elaborately controlled in considering $T_m$ value of hybridization between target sequences and probes, and also considering $T_m$ value of hairpin structure of undigested probes as well as $T_m$ value of hybridization between digested fragments and capture probes.

Therefore, there remain long-felt needs in the art to develop novel approaches for detection of a target sequence on a solid phase, particularly, being free from shortcomings of conventional technologies using tag sequence-carrying probes and capturing probes immobilized onto solid substrates.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences using a probing oligonucleotide (PO) and a capturing oligonucleotide (CO), in which target detection is accomplished by probe-cleavage reaction and additional probe-hybridization (i.e., 5' nucleolytic reaction of the PO and hybridization reaction between the cleaved/uncleaved PO and the CO). The present protocols with dramatically enhanced target specificity are well adopted to solid phase reactions, and ensures multiple detection of target sequences with more improved accuracy and convenience.

Therefore, it is an object of this invention to provide a method for detecting a target nucleic acid sequence from a DNA or a mixture of nucleic acids by a POCH (PO Cleavage and Hybridization) assay on a solid substrate.

It is another object of this invention to provide a kit for detecting a target nucleic acid sequence from a DNA or a mixture of nucleic acids by a POCH (PO Cleavage and Hybridization) assay on a solid substrate.

Other objects and advantages of the present invention will become apparent from the detailed description to follow taken in conjugation with the appended claims and drawings.

BRIEF DESCRIPTION OF THE DRAWINGS

FIG. 1 shows the schematic structures of PO (Probing Oligonucleotide) and CO (Capturing Oligonucleotide) used in a POCH (PO Cleavage and Hybridization) assay. The PO includes a non-tagged PO and a tagged PO that is then classified into a 3'-tagged PO and a 5'-tagged PO. Preferably, the 3'-end of the PO is blocked to prohibit its extension (FIG. 1A). The CO comprises a nucleotide sequence hybridizable with the PO. The CO is immobilized onto the solid substrate via its 3'-end or 5'-end. Preferably, the 3'-end of the CO immobilized via 5'-end is blocked to prohibit its extension (FIG. 1B).

FIG. 2 schematically represents the POCH assay using a non-tagged PO having a single fluorescent label at the 5'-end of its targeting portion.

FIG. 3 schematically represents the POCH assay using a non-tagged PO having a single fluorescent label at the 3'-end of its targeting portion.

FIG. 4 schematically represents the POCH assay using a 3'-tagged PO having a single fluorescent label at the 5'-end of its targeting portion.

FIG. 5 schematically represents the POCH assay using a 5'-tagged PO having a single fluorescent label at the 3'-end of its targeting portion.

FIG. 6 schematically represents the POCH assay using a 5'-tagged PO having a single fluorescent label at the 3'-end of its targeting portion and a CO further comprising a templating portion serving as a template for extension of the tagging portion hybridized with the CO.

FIG. 7 schematically represents the POCH assay using a non-tagged PO having a donor molecule and an acceptor molecule of an interactive dual label for measuring signal from the acceptor molecule. The donor molecule and the acceptor molecule are located to the extent that a signal from the donor molecule is quenched by the acceptor molecule when the uncleaved PO/CO duplex is formed.

FIG. 8 schematically represents the POCH assay using a 3'-tagged PO having a donor molecule and an acceptor molecule of an interactive dual label for measuring signal from the acceptor molecule. The donor molecule and the acceptor molecule are located to the extent that a signal from the donor molecule is quenched by the acceptor molecule when the uncleaved PO/CO duplex is formed.

FIG. 9 schematically represents the POCH assay using a 5'-tagged PO having a donor molecule and an acceptor molecule of an interactive dual label for measuring signal from the acceptor molecule. The donor molecule and the acceptor molecule are located to the extent that a signal from the donor molecule is quenched by the acceptor molecule when the uncleaved PO/CO duplex is formed.

FIG. 10 schematically represents the POCH assay using a non-tagged PO having a donor molecule and an acceptor molecule of an interactive dual label for measuring signal from the donor molecule. The donor molecule and the acceptor molecule are located to the extent that a signal from the donor molecule is unquenched by the acceptor molecule when the uncleaved PO/CO duplex is formed.

FIG. 11 schematically represents the POCH assay using a 3'-tagged PO having a donor molecule and an acceptor molecule of an interactive dual label for measuring signal from the donor molecule. The donor molecule and the acceptor molecule are located to the extent that a signal from the donor molecule is quenched by the acceptor molecule when the uncleaved PO/CO duplex is formed.

FIG. 12 schematically represents the POCH assay using a 5'-tagged PO having a donor molecule and an acceptor molecule of an interactive dual label for measuring signal from the donor molecule. The donor molecule and the acceptor molecule are located to the extent that a signal from the donor molecule is quenched by the acceptor molecule when the uncleaved PO/CO duplex is formed.

FIG. 13 schematically represents the POCH assay using an intercalating agent.

FIG. 14 represents the results of target detection by the POCH assay using a non-tagged PO with a single label.

FIG. 15 represents the results of target detection by the POCH assay using a 3'-tagged PO with a single label.

FIG. 16 represents the results of target detection by the POCH assay using a 5'-tagged PO with a single label.

FIG. 17 represents the results of target detection by the POCH assay using a 3'-tagged PO with a dual label.

FIG. 18 represents the results of target detection by the POCH assay with PCR amplification. PO is a non-tagged PO with a single label.

FIG. 19 represents the results of target detection by the POCH assay with PCR amplification. PO is a 3'-tagged PO with a single label.

FIG. 20 represents the results of real-time detection of target nucleic acid sequences by the POCH assay using a 3'-tagged PO with a single label.

DETAILED DESCRIPTION OF THIS INVENTION

Figure 20A:
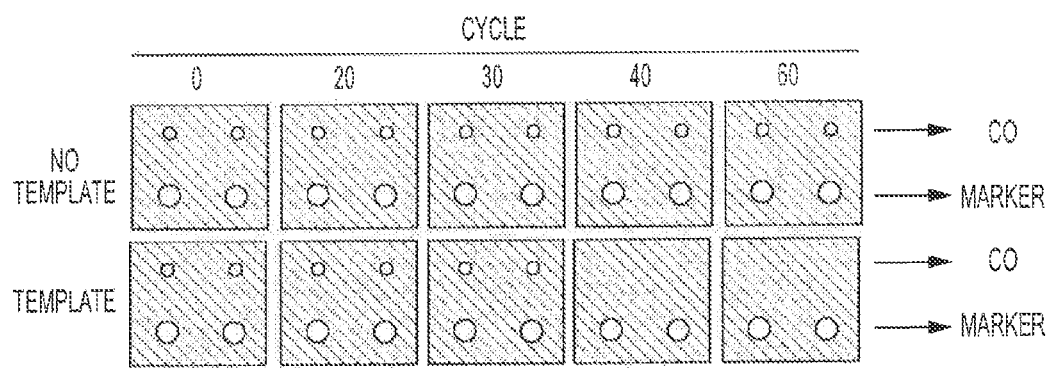
FIG. 20A shows fluorescent images depending on cycle numbers during the POCH assay and FIG. 20B shows change of fluorescence intensity depending on cycle numbers during the POCH assay.

The present inventors have made intensive researches to develop novel approaches to detect target sequences with more improved accuracy and convenience, inter alia, in a multiplex manner. As a result, we have established novel protocols for detection of target sequences using a probing oligonucleotide (PO) and a capturing oligonucleotide (CO), in which target detection is accomplished by probe-cleavage reaction and additional probe-hybridization (i.e., 5' nucleolytic reaction of the PO and hybridization reaction between the cleaved/uncleaved PO and the CO). The present protocols with dramatically enhanced target specificity are well adopted to solid phase reactions, and ensures multiple detection of target sequences with more improved accuracy and convenience.

The present invention is a novel protocol to detect target sequences on a solid substrate by utilizing a combination of PO and CO.

The underlying principle of the present invention is to detect occurrence of cleavage of the PO by using the CO immobilized on a solid substrate. In addition, it is noteworthy that where a target sequence in a sample is absent, an uncleaved PO is hybridized with the CO immobilized on a solid substrate. According to the present invention, a final signal to be measured is different depending on whether an uncleaved PO/CO duplex is formed or not, which is capable of indicating the presence or absence of the target sequence.

The present invention detects a target sequence in accordance with the performance principle described above, and is classified into three embodiments depending on adopted label systems.

The present invention will be described hereinbelow in more detail:

I. Target Detection Process by POCH Using Single Label

In one aspect of the present invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with an upstream oligonucleotide and a probing oligonucleotide (PO); wherein the upstream oligonucleotide comprises a hybridizing nucleotide sequence complementary to the target nucleic acid sequence; the PO comprises a targeting portion comprising a hybridizing nucleotide sequence complementary to the target nucleic acid sequence; the PO has a single label; the upstream oligonucleotide is located upstream of the PO; the upstream oligonucleotide or its extended strand induces cleavage of the PO by an enzyme having a 5' nuclease activity;

(b) contacting the resultant of the step (a) to the enzyme having the 5' nuclease activity under conditions for cleavage of the PO; wherein when the PO is hybridized with the target nucleic acid sequence, the PO is cleaved by the enzyme having the 5' nuclease activity to produce a single label-containing fragment;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex; and (d) detecting occurrence of the cleavage of the PO by measuring a signal from the single label on the solid substrate; whereby the occurrence of the PO cleavage indicates the presence of the target nucleic acid sequence.

It has been suggested that the presence of a target sequence is determined by hybridization of the cleaved fragment of a target probe with an oligonucleotide immobilized on a solid substrate (see U.S. Pat. Appln. Pub. Nos. 2008-0241838 and 2008-0193940). The conventional method determines the presence or absence of a target sequence by hybridizing only cleaved probe with the oligonucleotide immobilized on a solid substrate. The uncleaved probe is not involved in hybridization with the immobilized oligonucleotide. For this performance, the conventional method is required to prevent the uncleaved target probe from hybridizing with the immobilized oligonucleotide by designing the target probe with a tagging portion to have a hairpin structure or by controlling immobilization orientation of the immobilized oligonucleotide and its distance from the surface of a solid substrate.

The conventional method demanding the target probe having a hairpin structure has serious shortcomings in which the design of the target probe and reaction conditions have to be determined with considering both conditions for hybridization between the target probe having a hairpin structure and the target sequence and conditions for non-hybridization between the target probe and the immobilized oligonucleotide. Therefore, the conventional methods are very inconvenient and non-practical in terms of designing a target probe and an immobilized oligonucleotide and determination of reaction conditions.

In contrast to the conventional methods, the present invention employs hybridization between uncleaved PO and immobilized CO, being free from shortcomings associated with the conventional methods.

According to the present invention, a final signal to be measured indicative of the presence or absence of a target sequence is different depending on whether the cleaved fragment of PO is hybridized with CO immobilized on a solid substrate or the uncleaved PO is hybridized with immobilized CO.

Therefore, the present invention is named "PO Cleavage and Hybridization (POCH) analysis".

The present invention will be described in more detail as follows:

Step (a): Hybridization of an Upstream Oligonucleotide and a PO with a Target Nucleic Acid Sequence According to the present invention, a target nucleic acid sequence is first hybridized with an upstream oligonucleotide and a PO (Probing Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

According to a preferred embodiment, the upstream oligonucleotide is an upstream primer or an upstream probe.

The PO used in the present invention is preferably a probe.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. Preferably, the primer is single-stranded deoxyribonucleotide molecules.

The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of target nucleic acid sequences with the upstream oligonucleotide and the PO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PO) and target nucleotide sequences. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The probing oligonucleotide (PO) used herein means an oligonucleotide comprising a targeting portion serving as a probe.

According to a preferred embodiment, the PO includes a non-tagged PO without a tagging portion having a nucleotide sequence non-complementary to the target nucleic acid sequence and a tagged PO with a tagging portion having a nucleotide sequence non-complementary to the target nucleic acid sequence (FIG. 1A).

According to a preferred embodiment, the PO is a 3'-tagged PO further comprising in its 3'-portion a tagging portion having a nucleotide sequence non-complementary to the target nucleic acid sequence or a 5'-tagged PO further comprising in its 5'-portion a tagging portion having a nucleotide sequence non-complementary to the target nucleic acid sequence (FIG. 1A).

The tagging portion of the PO preferably has a tagging portion having a nucleotide sequence non-complementary to the target nucleic acid sequence. The term "non-complementary" is used herein to mean that primers or probes are sufficiently non-complementary to not hybridize selectively to a target nucleic acid sequence under the designated annealing conditions or stringent conditions, encompassing the terms "substantially non-complementary" and "perfectly non-complementary", preferably perfectly non-complementary.

Preferably, the tagged PO is utilized to hybridize selectively with the CO through the tagging portion.

The PO does not require any specific lengths. The non-tagged PO may have any lengths so long as it is specifically hybridized with the target nucleic acid sequence, for example, its length may be 10-60 nucleotides, 10-50 nucleotides, 10-40 nucleotides, 10-30 nucleotides, 15-60 nucleotides, 15-50 nucleotides, 15-40 nucleotides, 15-30 nucleotides, 20-60 nucleotides, 20-50 nucleotides, 20-40 nucleotides or 20-30 nucleotides. The tagged PO may be 15-80 nucleotides, 15-60 nucleotides, 15-40 nucleotides, 20-80 nucleotides, 20-60 nucleotides, 20-40 nucleotides, 30-80 nucleotides, 30-60 nucleotides, or 30-40 nucleotides in length. The targeting portion of the PO may be in any lengths so long as it is specifically hybridized with target nucleic acid sequences. For example, the targeting portion of the PO may be 10-50 nucleotides, 10-40 nucleotides, 10-30 nucleotides, 15-50 nucleotides, 15-40 nucleotides, 15-30 nucleotides, 20-50 nucleotides, 20-40 nucleotides or 20-30 nucleotides in length. The tagging portion of the tagged PO may be in any lengths so long as it is specifically hybridized with the CO. For instance, the tagging portion of the PO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PO may have a 3'-OH terminal. Preferably, the 3'-end of the PO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PO may be designed to have a secondary structure such as a hairpin structure. Since an uncleaved PO is hybridized with oligonucleotides immobilized on a solid substrate in the present invention, the hairpin structure has to be designed not to prevent the uncleaved PO from hybridization with immobilized CO. Preferably, the hairpin structure of the PO has lower $T_m$ value than that of duplex between the uncleaved PO and immobilized CO.

Meanwhile, according to the conventional method to detect a target sequence by use of cleavage reaction of a target probe having a tagging portion and hybridization with an oligonucleotide immobilized on a solid substrate, it is required that the target probe has a hairpin structure to prevent an uncleaved target probe from hybridizing with the immobilized oligonucleotide.

Where the tagged PO is used, the hybridization with the target nucleic acid sequence is performed under stringent conditions that its targeting portion is hybridized with the target nucleic acid sequence and its tagging portion is not hybridized with the target nucleic acid sequence. The phrase, "the tagging portion of the PO is not hybridized with the target nucleic acid sequence" means that it does not form stable duplex with the target nucleic acid sequence under certain stringent condition. Preferably, the tagging portion of the tagged PO is not hybridized with the target nucleic acid sequence, forming a single strand.

The upstream oligonucleotide is located upstream of the PO when it hybridizes with the target nucleic acid. The upstream oligonucleotide or its extended strand hybridized with the target nucleic acid sequence induces cleavage of the PO hybridized with the target nucleic acid sequence by an enzyme having a 5' nuclease activity.

The induction of the PO cleavage by the upstream oligonucleotide may be accomplished by two fashions: (i) upstream oligonucleotide extension (i.e., polymerization)-independent cleavage induction; and (ii) upstream oligonucleotide extension-dependent cleavage induction.

Where the upstream oligonucleotide is positioned adjacently to the PO sufficient to induce the PO cleavage by an enzyme having a 5' nuclease activity, the enzyme bound to the upstream oligonucleotide digests the PO with no extension reaction. In contrast, where the upstream oligonucleotide is positioned distantly to the PO, an enzyme having a polymerase activity (e.g., template-dependent polymerase) catalyzes extension of the upstream oligonucleotide (e.g., upstream primer) and an enzyme having a 5' nuclease activity bound to the extended product digests the PO.

Therefore, the upstream oligonucleotide may be located relatively to the PO in two fashions. The upstream oligonucleotide may be located adjacently to the PO sufficient to induce the PO cleavage in an extension (i.e., polymerization)-independent manner. Alternatively, the upstream oligonucleotide may be located distantly to the PO sufficient to induce the PO cleavage in an extension-dependent manner.

The term used herein "adjacent" with referring to positions or locations means that the upstream oligonucleotide is located adjacently to the targeting portion of the PO to form a nick. Also, the term means that the upstream oligonucleotide is located 1-30 nucleotides, 1-20 nucleotides or 1-15 nucleotides apart from the targeting portion of the PO.

According to a preferred embodiment, the upstream oligonucleotide is located distantly to the PO sufficient to induce the PO cleavage in an extension-dependent manner.

The term used herein "distant" with referring to positions or locations has no limitations as the term "adjacent", including any positions or locations sufficient to ensure extension reactions. For example, the term "distant" may include location to form a nick.

According to a preferred embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide has a partial-overlapped sequence with the targeting portion of the PO. Preferably, the overlapped sequence is 1-10 nucleotides, more preferably 1-5 nucleotides, still more preferably 1-3 nucleotides in length. Where the 5'-tagged PO having the partial-overlapped sequence is used, the 3'-targeting portion may be partially digested together with digestion of the tagging portion in the cleavage reaction of the step (b). In addition, the overlapped sequence permits to cleave a desired site of the targeting portion.

According to a preferred embodiment, the upstream primer induces through its extended strand the cleavage of the PO by the enzyme having the 5' nuclease activity.

The conventional technologies for cleavage reactions by upstream oligonucleotides may be applied to the present invention, so long as the upstream oligonucleotide induces cleavage of the PO hybridized with the target nucleic acid sequence. For example, methods disclosed in U.S. Pat. Nos. 5,210,015, 5,487,972, 5,691,142, 5,994,069 and 7,381,532 and U.S. Appln. Pub. No. 2008-0241838 may be applied to the present invention.

According to a preferred embodiment, the present method is performed in the presence of a downstream primer. The downstream primer generates additionally the target nucleic acid sequence to be hybridized with the PO, enhancing sensitivity in target detection.

Where the downstream primer is additionally used, a secondary PO located downstream of the downstream primer is additionally used.

According to a preferred embodiment, when the upstream primer and the downstream primer are used, a template-dependent nucleic acid polymerase is employed for extension of the primers. The template-dependent nucleic acid polymerase may serve as an enzyme having a 5' nuclease activity for cleavage of the PO.

According to a preferred embodiment, the upstream oligonucleotide (upstream primer or upstream probe) and/or the downstream primer have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35: 6e40(2007)).

According to a preferred embodiment, the targeting portion of the PO has a modified dual specificity oligonucleotide (mDSO) structure developed by the present inventor. The modified dual specificity oligonucleotide (mDSO) structure shows significantly improved target specificity compared with conventional probes (see WO 2011/028041).

The term "conventional oligonucleotide" refers to oligonucleotides (primer or probe) having no DSO or mDSO structure.

The PO used in this invention has a single label. The single label provides signal indicative of the presence or absence of the target nucleic acid sequence. The label will be described in more detail in the step (d).

Step (b): Cleavage of the PO

Afterwards, the resultant of the step (a) is contacted to an enzyme having a 5' nuclease activity under conditions for cleavage of the PO.

The PO hybridized with the target nucleic acid sequence is digested by the enzyme having the 5' nuclease activity to release a single label-containing fragment (see FIGS. 2-6). Where the target nucleic acid sequence is absent, the PO is not digested by the enzyme having the 5' nuclease activity.

The term used herein "conditions for cleavage of the PO" means conditions sufficient to digest the PO hybridized with the target nucleic acid sequence by the enzyme having the 5' nuclease activity, such as temperature, pH, ionic strength, buffer, length and sequence of oligonucleotides, and enzymes. For example, when Taq DNA polymerase is used as the enzyme having the 5' nuclease activity, the conditions for cleavage of the PO include Tris-HCl buffer, KCl, MgCl$_2$ and temperature.

A multitude of conventional technologies may be employed for the cleavage reaction of the PO. The cleavage sites of the PO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

The length and sequence of the single label-containing fragment may be varied depending on adopted cleavage technology. In particular, where the tagged PO is used, its fragment comprising a partial or all sequence of the tagging portion may be produced. With adjusting the location of the single label on the tagged PO, the single label may be not existed on the fragment comprising a partial or all sequence of the tagging portion.

Generally, the initial site for the cleavage of the PO by extension of the upstream primer is a starting point of the double strand between the PO and the target nucleic acid sequence or a site 1-3 nucleotides apart from the starting point. The cleaved PO becomes shorter in length so that it is dissociated from the target nucleic acid sequence. Where the 3'-tagged PO or the 5'-tagged PO is used, a fragment comprising the tagging portion and a part of the targeting portion may be produced. When a cleavage reaction independent on extension of upstream oligonucleotides is employed, the cleavage site of the PO is determined depending on location of upstream oligonucleotides. Where the 3'-tagged PO or the 5'-tagged PO is used, a fragment of the PO produced may comprise (i) a part of the tagging portion, (ii) the tagging portion or (iii) the tagging portion and a part of the targeting portion.

The term used herein "a fragment comprising the tagging portion or a part of the tagging portion" in conjunction with cleavage of the tagged PO by the enzyme having the 5' nuclease activity is used to encompass (i) the tagging portion, (ii) the tagging portion and an adjacent partial sequence of the targeting portion and (iii) a part of the tagging portion.

The term "part" used in conjunction with the PO such as the part of the 5'-tagging portion of the PO and the 5'-end part of the 3'-targeting portion of the PO refers to a nucleotide sequence composed of 1-40, 1-30, 1-20, 1-15, 1-10 or 1-5 nucleotides, preferably 1, 2, 3 or 4 nucleotides.

According to a preferred embodiment, the enzyme having the 5' nuclease activity is DNA polymerase having a 5' nuclease activity or FEN nuclease, more preferably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus sllvanus*, *Thermus* species Z05, *Thermus* species sps 17, *Thermus thermophllus*, *Thermotoga maritima*, *Thermotoga neapolitana*, *Thermosipho africanus*, *Thermococcus Thermococcus barossi*, *Thermococcus gorgonarius*, *Thermotoga maritima*, *Thermotoga neapolitana*, *Therm osiphoafricanus*, *Pyrococcus woesei*, *Pyrococcus horikoshii*, *Pyrococcus abyssi*, *Pyrodictium occultum*, *Aquifex pyrophllus* and *Aquifex aeolieus*. Most preferably, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus*, *Pyrobaculum aerophilum*, *Thermococcus litoralis*, *Archaeaglobus veneficus*, *Archaeaglobus profundus*, *Acidianus brierlyi*, *Acidianus ambivalens*, *Desulfurococcus amylolyticus*, *Desulfurococcus mobilis*, *Pyrodictium brockii*, *Thermococcus gorgonarius*, *Thermococcus zilligii*, *Methanopyrus kandleri*, *Methanococcus igneus*, *Pyrococcus horikoshii*, *Aeropyrum pernix*, and *Archaeaglobus veneficus*.

Where the upstream primer is used in the step (a), it is preferable that the conditions for cleavage of the PO comprise extension reaction of the upstream primer.

According to a preferred embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization with CO on Solid Phase

The resultant of the step (b) is contacted to a CO (Capturing Oligonucleotide) immobilized onto the solid substrate for hybridization reaction.

In the present invention, the cleavage of the PO is detected by use of the CO immobilized onto the solid substrate. Where the PO is not cleaved in the step (b), the single label-containing uncleaved PO is hybridized with the CO immobilized onto the solid substrate such that signal on the solid substrate is provided by the single label. Where the PO is cleaved in the step (b), the single label-containing cleaved fragment is not hybridized with the CO such that signal on the solid substrate is not provided by the single label.

Since the occurrence of cleavage of the PO is dependent on the presence of the target nucleic acid sequence, the target nucleic acid sequence may be detected by measuring extinction or reduction of signal from the single label on the solid substrate.

The CO comprises a nucleotide sequence hybridizable with the PO. The term used herein or "hybridizable sequence" in conjunction with the CO refers to a sequence capable of forming a stable duplex with the uncleaved PO in the step (c). For instance, a hybridizable sequence of the CO with the PO may comprise a complementary sequence to all or a part of the targeting portion of the PO; all or a part of the tagging portion of the PO; all of the targeting portion and a part of the tagging portion of the PO; a part of the targeting portion and all of the tagging portion of the PO; or a part of the targeting portion and a part of the tagging portion of the PO.

There is no intended distinction between the terms "nucleotide sequence hybridizable" and "nucleotide sequence complementary", and these terms will be used interchangeably.

The hybridization reaction in the step (c) is performed under conditions such that the single label-containing fragment is not hybridized with the CO and the uncleaved PO is hybridized with the CO to form an uncleaved PO/CO duplex.

In an embodiment of this invention, the CO comprises a nucleotide sequence hybridizable with the targeting portion of the PO. The nucleotide sequence hybridizable with the targeting portion of the PO comprises a complementary sequence to all or a part of the targeting portion of the PO and has complementarity and length sufficient to stably form a duplex between the uncleaved PO and the CO in the hybridization reaction of the step (c).

As illustrated in FIGS. 2 and 3, the CO comprises a nucleotide sequence hybridizable with the targeting portion of the PO. Where the target nucleic acid sequence is present, the single label-containing fragment generated by the cleavage reaction has shorter length than the uncleaved PO and then is not able to hybridize with the CO under certain stringent conditions (particularly, temperature). Finally, the single label does not exist on the solid substrate.

Alternatively, the CO may be designed not to have a hybridizable sequence with the single label-containing fragment for preventing the single label-containing fragment from hybridization with the CO.

Therefore, when the target nucleic acid sequence is present, the duplex between the uncleaved PO and the CO is not generated and no signal is provided from the single label.

Where the target nucleic acid sequence is absent, the uncleaved PO forms a duplex with the CO and the single label exists on the solid substrate.

If the illustrated processes in FIGS. 2 and 3 are performed using a polymerase having no 5' nuclease activity, the non-tagged PO hybridized with the target nucleic acid sequence is not cleaved. Since the non-tagged PO is hybridized with the target nucleic acid sequence, its hybridization with the CO may be prevented under a delicately controlled condition, providing no signal from the single label. However, in the case of using enzymes having a 5' nuclease activity as the present invention, the PO hybridized with the target nucleic acid sequence is cleaved and the occurrence of the cleavage is measured under a conveniently established condition to accurately detect the presence of the target nucleic acid sequence.

As illustrated in FIGS. 4 and 5, the CO comprises a nucleotide sequence hybridizable with the tagging portion of the PO. The single label on the tagged PO is positioned such that the single label is not remained on the tagging portion-containing fragment released by cleavage of the tagged PO and hybridized with the CO. Even when the tagging portion-containing fragment is hybridized with the CO, no signal is provided the single label because the tagging portion-containing fragment does not carry the single label. Signal is provided upon hybridization of the uncleaved tagged-PO with the CO.

Where the target nucleic acid sequence is present, the duplex between the uncleaved PO and the CO is not formed due to cleavage of the PO, resulting in extinction (or reduction) of signal from the single label on the solid substrate that is indicative of the presence of the target nucleic acid sequence.

According to a preferred embodiment using the tagged PO, the nucleotide sequence of the CO hybridizable with the tagging portion of the PO comprises a complementary sequence to all or a part of the tagging portion of the PO and has complementarity and length sufficient to stably form a duplex between the uncleaved tagged-PO and the CO in the hybridization reaction of the step (c).

Alternatively, where the tagged PO is used, the CO may comprise a nucleotide sequence hybridizable with a part (or all) of the tagging portion and a part (or all) of the targeting portion of the tagged PO. The position of the single label on the tagged PO is determined with considering cleavage method, cleavage site and the sequence of the CO, and the cleavage of the tagged PO is carried out under conditions that the single label-containing fragment is not hybridized with the CO. Preferably, the single label is positioned such that it is remained on a fragment released by cleavage of the tagged PO and not hybridized with the CO.

According to a preferred embodiment using the 5'-tagged PO, the CO may further comprise a templating portion serving as a template for extension of the tagging portion hybridized with the CO (see FIG. 6). The extension product enables hybridization with the CO to be more stable. For the extension, an additional DNA polymerase may be needed.

The CO is immobilized onto the solid substrate through its 5'-end or 3'-end.

According to a preferred embodiment, the PO is the 3'-tagged PO and the CO is immobilized onto the solid substrate through its 5'-end (FIG. 4). Preferably, the PO is the 5'-tagged PO and the CO is immobilized onto the solid substrate through its 3'-end (FIG. 5).

According to a preferred embodiment, the solid substrate on which the CO is immobilized is a microarray. The CO is immobilized directly or indirectly (preferably indirectly) through its 5'-end or 3'-end onto the surface of the solid substrate. Furthermore, the CO may be immobilized on the surface of the solid substrate in a covalent or non-covalent manner. Where the immobilized COs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for CO immobilization. In addition, poly (T) tail or poly (A) tail may be used as linkers. The poly (T) tail or poly (A) tail is advantageous in the senses that it is capable of decreasing space hindrance on enzyme action (e.g., enzymatic cleavage reaction) and increasing hybridization efficiency. The poly (T) tail or poly (A) tail is not considered as sequence of probes.

The microarray to provide a reaction environment in this invention may include any those known to one of skill in the art. All processes of the present invention, i.e., hybridization to target nucleic acid sequences, cleavage and detection are carried out on the microarray. The immobilized COs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. A plurality of immobilized COs in this invention may be immobilized on an addressable region or two or more addressable regions on a solid substrate that may comprise 2-1,000,000 addressable regions. Immobilized COs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because the labels on the COs immobilized are physically separated. In this regard, the number of target nucleic acid sequences to be detected by the present invention on the solid phase is not limited.

Using confocal detection devices on a solid phase, signal existed only on the solid substrate may be detected with no influence of signal from labels present in a reaction solution.

The length of the CO may be widely varied. The CO may have any length so long as it is capable of forming a duplex with the uncleaved PO. For example, the CO is 5-80 nucleotides, 5-60 nucleotides, 5-40 nucleotides, 5-30 nucleotides, 10-80 nucleotides, 10-60 nucleotides, 10-40 nucleotides, 10-30 nucleotides, 10-20 nucleotides, 15-80 nucleotides, 15-60 nucleotides, 15-40 nucleotides, 15-30 nucleotides or 15-20 nucleotides in length.

According to a preferred embodiment using the 5'-tagged PO, where the CO further comprises the templating portion for extension of the tagging portion hybridized with the CO, the CO may further comprise an additional length of 5-100 nucleotides in the templating portion.

According to a preferred embodiment, the 3'-end of the CO is blocked to prohibit its extension. The non-extendible blocking of the CO may be achieved in accordance with conventional methods. For instance, the blocking may be performed by adding to the 3'-hydroxyl group of the last nucleotide of the CO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The hybridization in the step (c) can be described in detail with referring to descriptions in the step (a).

The hybridization in the step (c) is performed under conditions such that the single label-containing fragment is not hybridized with the CO and an uncleaved PO is hybridized with the CO to form an uncleaved PO/CO duplex. The hybridization conditions may routinely be determined by conventional methods known to one of skill in the art. For example, the hybridization conditions may be adjusted by temperature, concentration of components, hybridization times, buffer components, and their pH and ionic strength.

According to a preferred embodiment, the hybridization conditions in the step (c) are adjusted by temperature for hybridization. Alternatively, the hybridization conditions in the step (c), in particular the conditions permitting the single label-containing fragment not to hybridize with the CO, may be provided by excluding in the CO a sequence being capable of stably hybridizing with the single label-containing fragment.

The PO and CO may be comprised of naturally occurring dNMPs. Alternatively, the PO and CO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PO and CO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

Step (d): Detection of PO Cleavage Indicating the Presence of Target Sequence

Following the hybridization reaction, occurrence of the cleavage of the PO is detected by measuring a signal from the single label on the solid substrate, whereby the occurrence of the PO cleavage indicates the presence of the target nucleic acid sequence.

As discussed above, the hybridization pattern of the PO with the CO is distinctly different depending on cleavage of the PO. Such difference in the hybridization pattern is responsible for difference in signal on the solid substrate. Therefore, the present or absence of the target nucleic acid sequence may be determined by detecting the signal from the single label on the solid substrate.

The step (d) is carried out by measuring the signal from the single label bound to the PO on the solid substrate.

The single label on the PO may be described as a reporter molecule. The single label used includes, but not limited to, chemical labels (e.g., biotin), enzymatic labels (e.g., alkaline phosphatase, peroxidase, β-galactosidase and β-glucosidase), fluorescent labels, luminescent labels, chemiluminescent labels, electrochemical labels and metal labels. Preferably, the single label includes fluorescent labels.

The single label is positioned such that the single label is not remained on a fragment which is released by cleavage of PO and hybridized with the CO.

Where the non-tagged PO is used, the single label may be linked to any site. Preferably, the single label is linked to a 5'-end portion or a 3'-end portion of the non-tagged PO. More preferably, it is located at the 5'-end or 3'-end or at 1-20 nucleotides (still more preferably 1-10 nucleotides) apart from the 5'-end or 3'-end of the non-tagged PO, still more preferably, at the 5'-end or 3'-end.

According to a preferred embodiment using the tagged PO, the single label is positioned such that the single label is not remained on a tagging portion-containing fragment released by cleavage of the tagged PO. More preferably, the single label is positioned such that the single label is not remained on a tagging portion-containing fragment which is released by cleavage of the tagged PO and hybridized with the CO.

The location of the single label may be determined with considering cleavage methods, cleavage sites, and release of the cleaved PO from the target nucleic acid sequence.

More preferably, the single label is located on a 5'-end portion or at 1-20 nucleotides (still more preferably 1-10 nucleotides) apart from the 5'-end of the 3'-tagged PO, and located on a 3'-end portion or at 1-20 nucleotides (still more preferably 1-10 nucleotides) apart from the 3'-end of the 5'-tagged PO. Still more preferably, the single label is located on the 5'-end of the 3'-tagged PO, and located on the 3'-end of the 5'-tagged PO.

According to a preferred embodiment, the tagged PO has the single label; the single label is positioned on the targeting portion of the tagged PO; the single label is positioned such that the single label is not remained on the tagging portion-containing fragment generated by the cleavage of the PO in the step (b); and the duplex between the tagging portion-containing fragment and the CO does not have the single label and the uncleaved PO/CO duplex has the single label (see FIGS. 4 and 5). The tagging portion-containing fragment/CO duplex immobilized on the solid substrate fails to provide the signal due to the absence of the single label; however the uncleaved PO/CO duplex provides the signal due to the presence of the single label on the uncleaved PO.

As described above, the presence of the target nucleic acid sequence is detected by measuring the signal from the single label on the solid substrate.

According to a preferred embodiment using the PO with the single label, the signal finally measured is compared with signal from a negative control having no target nucleic acid sequence. The extinction (or reduction) of the signal is then determined to detect the target nucleic acid sequence.

According to a preferred embodiment using the PO with the single label, where the detection on the solid substrate is continuously performed along with repetition of cleavage of the POs, the number of the POs cleaved is increased upon the repetition number of the cleavage reaction and the signal is decreased in parallel with the number of the POs cleaved. Then, the target nucleic acid sequence can be detected in a real-time manner. In contrast, the change of the signal is not observed in the absence of the target nucleic acid sequence.

The single fluorescent labels useful in the present invention may include any molecules known in the art. Examples of those are: Cy2™ (506), YO-PRO™-1 (509), YOYO™-1 (509), Calcein (517), FITC (518), Fluor X™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the single fluorescent labels include JOE, FAM, TAMRA, ROX and fluorescein-based label.

The single label may be linked to the PO by a variety of methods known to one of skill in the art. Preferably, the single label may be linked to the PO via a spacer containing at least three carbon atoms (e.g., 3-carbon spacer, 6-carbon spacer and 12-carbon spacer).

II. Target Detection Process by POCH Using Dual Label

The present invention exhibits excellent performance using an interactive dual label in detection of the target nucleic acid sequence.

In another aspect of this invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with an upstream oligonucleotide and a probing oligonucleotide (PO); wherein the upstream oligonucleotide comprises a hybridizing nucleotide sequence complementary to the target nucleic acid sequence; the PO comprises a targeting portion comprising a hybridizing nucleotide sequence complementary to the target nucleic acid sequence; the PO has an interactive dual label comprising a donor molecule and an acceptor molecule; the upstream oligonucleotide is located upstream of the PO; the upstream oligonucleotide or its extended strand induces cleavage of the PO by an enzyme having a 5' nuclease activity;

(b) contacting the resultant of the step (a) to the enzyme having the 5' nuclease activity under conditions for cleavage of the PO; wherein when the PO is hybridized with the target nucleic acid sequence, the PO is cleaved by the enzyme having the 5' nuclease activity to separate the interactive dual label, whereby a donor-containing fragment and an acceptor-containing fragment are produced;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that at least one of the donor-containing fragment and the acceptor-containing fragment is not hybridized with the CO and an uncleaved PO is hybridized with the CO to form an uncleaved PO/CO duplex; wherein a signal from the uncleaved PO/CO duplex is differentiated from a signal provided at the time that at least one of the donor-containing fragment and the acceptor-containing fragment is not hybridized with the CO; and (d) detecting occurrence of the cleavage of the PO by measuring a signal from the interactive dual label on the solid substrate; whereby the occurrence of the PO cleavage indicates the presence of the target nucleic acid sequence.

Since the second embodiment of this invention is the same as the first embodiment using the single label except for a label system, the common descriptions between them are omitted in order to avoid undue redundancy leading to the complexity of this specification.

The donor/acceptor interactive dual label is linked to the PO.

The interactive dual label is a signal generating system in which energy is passed non-radioactively between a donor molecule and an acceptor molecule. As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

According to a preferred embodiment, the PO has an interactive dual label, more preferably a FRET label, still more preferably a dual label comprising a donor molecule and an acceptor molecule (see FIGS. 7-13).

The donor molecule and the acceptor molecule useful in this invention include any molecules known to one skilled in the art and their examples may be described with referring to fluorescent labels described above.

Suitable pairs of donor-acceptor are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992);

Pringsheim, Fluorescence and Phosphorescence (Interscience Publishers, New York, 1949); Haugland, R. P., Handbook of Fluorescent Probes and Research Chemicals, 6$^{th}$ Edition (Molecular Probes, Eugene, Oreg., 1996) U.S. Pat. Nos. 3,996,345 and 4,351,760.

In the signaling system comprising a reporter and a quencher adopted to the PO, the reporter encompasses a donor of FRET and the quencher encompasses the other partner (acceptor) of FRET. For example, a fluorescein dye is used as the reporter and a rhodamine dye as the quencher.

The donor (reporter) molecule and the acceptor (quencher) molecule linked to the PO may be fluorescent or non-fluorescent. For example, a non-fluorescent dark quencher capable of quenching fluorescence with broader wavelength range or a specific wavelength may be used in this invention. Where the acceptor (quencher) molecule is fluorescent, signal from the fluorescent acceptor (quencher) molecule may be employed to detect the target nucleic acid sequence.

The present invention will be described in more detail as follows:

Step (a): Hybridization of an Upstream Oligonucleotide and a PO with a Target Nucleic Acid Sequence The step (a) of the second embodiment of this invention can be understood with reference to descriptions for the step (a) of the first embodiment.

The PO has an interactive dual label comprising a donor molecule and an acceptor molecule that provides signal indicative of the presence of the target nucleic acid sequence.

Step (b): Cleavage of the PO

The step (b) of the second embodiment of this invention can be understood with reference to descriptions for the step (b) of the first embodiment.

The resultant of the step (a) is contacted to an enzyme having a 5' nuclease activity under conditions for cleavage of the PO.

The PO hybridized with the target nucleic acid sequence is digested by the enzyme having the 5' nuclease activity to separate the interactive dual label, whereby a donor-containing fragment and an acceptor-containing fragment are produced (see FIGS. 7-13).

According to a preferred embodiment, the donor molecule and the acceptor molecule on the PO are separated by a cleavage site by the enzyme having the 5' nuclease activity.

In the absence of the target nucleic acid sequence, the PO is not digested by the enzyme having the 5' nuclease activity and the interactive dual label is therefore not separated.

Step (c): Hybridization with CO on Solid Phase

The resultant of the step (b) is contacted to a CO (Capturing Oligonucleotide) immobilized onto the solid substrate for hybridization reaction.

The step (c) of the second embodiment of this invention can be understood with reference to descriptions for the step (c) of the first embodiment. The hybridization reaction is performed under conditions such that at least one of the donor-containing fragment and the acceptor-containing fragment is not hybridized with the CO and an uncleaved PO is hybridized with the CO to form an uncleaved PO/CO duplex. The hybridization conditions may routinely be determined by conventional methods known to one of skill in the art. For example, the hybridization conditions may be adjusted by temperature, concentration of components, hybridization times, buffer components, and their pH and ionic strength.

According to a preferred embodiment, the hybridization conditions such that at least one of the donor-containing fragment and the acceptor-containing fragment is not hybridized with the CO are adjusted by temperature for hybridization. Alternatively, the hybridization conditions in the step (c) may be provided by excluding in the CO a sequence being capable of stably hybridizing with the label-containing fragment.

Where the target nucleic acid sequence is present, at least one of the donor-containing fragment and the acceptor-containing fragment is not hybridized with the CO. In the case of the absence of the target nucleic acid sequence, the uncleaved PO having the interactive dual label is hybridized with the CO.

Signal provided from the uncleaved PO/CO duplex (i.e., in the absence of the target nucleic acid sequence) is distinctly differentiated from a signal provided at the time that at least one of the donor-containing fragment and the acceptor-containing fragment is not hybridized with the CO (i.e., in the presence of the target nucleic acid sequence). Therefore, signal from the interactive dual label is differently generated depending on the presence or absence of the target nucleic acid sequence.

Step (d): Detection of PO Cleavage Indicating the Presence of Target Sequence

Following the hybridization reaction, occurrence of the cleavage of the PO is detected by measuring a signal from the interactive dual label on the solid substrate, whereby the occurrence of the PO cleavage indicates the presence of the target nucleic acid sequence.

As discussed above, the hybridization pattern of the PO with the CO is distinctly different depending on cleavage of the PO. Such difference in the hybridization pattern is responsible for difference in signal on the solid substrate. Therefore, the present or absence of the target nucleic acid sequence may be determined by detecting the signal from the interactive dual label on the solid substrate.

In the case of using the interactive dual label, the signal is measured in two fashions. The first fashion is to measure signal generated from the acceptor molecule and the second fashion is to measure signal generated from the donor molecule.

The first measurement fashion is illustrated in FIGS. 7-9.

FIG. 7 using the non-tagged PO represents an embodiment to measure signal from the acceptor molecule. According to a preferred embodiment, the nucleotide sequence hybridizable with the PO in the CO comprises a nucleotide sequence hybridizable with the targeting portion of the PO. In this case, the interactive dual label is preferably located to the extent that signal from the donor molecule is quenched by the acceptor molecule when the uncleaved PO/CO duplex is formed, wherein the step (d) is performed by detecting signal from the acceptor molecule.

As exemplified in FIG. 7, where the donor molecule and the acceptor molecule are adjacent to each other on the non-tagged PO to the extent that energy is passed between the donor molecule and the acceptor molecule (e.g., adjacent to allow a FRET phenomenon), the non-tagged PO hybridized with the target nucleic acid sequence is cleaved to form a donor molecule-containing fragment and an acceptor molecule-containing fragment. Thus, the interaction between the donor molecule and the acceptor molecule does not occur unless both the donor molecule-containing fragment and the acceptor molecule-containing fragment are hybridized with the CO in the step (c), finally providing no signal on the solid substrate.

The expression used herein "the donor molecule and the acceptor molecule are adjacent" means that the donor molecule and the acceptor molecule are separated by a number of nucleotides in the probe to the extent that energy is passed between the donor molecule and the acceptor molecule. Preferably, the donor molecule and the acceptor molecule are separated by 1-20, 1-15 and 1-10 nucleotides.

In the event that the target nucleic acid sequence is absent, the uncleaved non-tagged PO is hybridized with the CO and the interaction between the donor molecule and the acceptor molecule occurs, thereby providing the signal from the acceptor molecule. Illumination of light with excitation wavelength for the donor molecule generates fluorescence from the donor molecule that is then quenched by the acceptor molecule, finally providing a fluorescent signal from the acceptor.

In the presence of the target nucleic acid sequence, the uncleaved PO/CO duplex is not formed due to cleavage of the PO and thus fails to provide the signal from the acceptor. The measurement of extinction (or reduction) of the single from the acceptor molecule on the solid substrate enables to determine the presence of the target nucleic acid sequence.

FIGS. 8 and 9 using the tagged PO represent embodiments to measure signal from the acceptor molecule. According to a preferred embodiment, the PO is a 3'-tagged PO further comprising in its 3'-portion a tagging portion having a nucleotide sequence non-complementary to the target nucleic acid sequence or a 5'-tagged PO further comprising in its 5'-portion a tagging portion having a nucleotide sequence non-complementary to the target nucleic acid sequence, and the nucleotide sequence hybridizable with the PO in the CO comprises a nucleotide sequence hybridizable with the tagging portion of the PO. The interactive dual label is preferably located to the extent that a signal from the donor molecule is quenched by the acceptor molecule when the uncleaved PO/CO duplex is formed, wherein the step (d) is performed by detecting a signal from the acceptor molecule.

As illustrated in FIG. 8 using the 3'-tagged PO, where the donor molecule and the acceptor molecule are conformationally adjacent to each other to the extent that energy is passed between the donor molecule and the acceptor molecule, the 3'-tagged PO hybridized with the target nucleic acid sequence is cleaved to form a donor molecule-containing fragment and an acceptor molecule-containing fragment. The acceptor molecule-containing fragment comprising the tagging portion is hybridized with the CO comprising a nucleotide sequence hybridizable with the tagging portion of the 3'-tagged PO but the donor molecule-containing fragment does not involve in hybridization with the CO, thus failing to provide the signal from the acceptor.

The expression used herein "the donor molecule and the acceptor molecule are conformationally adjacent" means that the donor molecule and the acceptor molecule are three-dimensionally adjacent to each other by a conformational structure of a part of PO or PO such as random coil and hairpin structure.

In the event that the target nucleic acid sequence is absent, the uncleaved 3'-tagged PO is hybridized with the CO and the interaction between the donor molecule and the acceptor molecule occurs, thereby providing the signal from the acceptor molecule.

In the presence of the target nucleic acid sequence, the uncleaved PO/CO duplex is not formed due to cleavage of the 3'-tagged PO and thus fails to provide the signal from the acceptor. The measurement of extinction (or reduction) of the single from the acceptor molecule on the solid substrate enables to determine the presence of the target nucleic acid sequence.

According to a preferred embodiment, the donor molecule and the acceptor molecule on the 3'-tagged PO are adjacent to each other to the extent that energy is passed between them. The donor molecule and the acceptor molecule are located to the 3'-tagged PO in a 5' to 3' direction or 3' to 5' direction.

According to a preferred embodiment, both the donor molecule and the acceptor molecule are located on the targeting portion of the 3'-tagged PO or one of them is located on the targeting portion and the other located on the tagging portion of the 3'-tagged PO.

As illustrated in FIG. 9 using the 5'-tagged PO, where the donor molecule and the acceptor molecule are conformationally adjacent to each other to the extent that energy is passed between the donor molecule and the acceptor molecule, the 5'-tagged PO hybridized with the target nucleic acid sequence is cleaved to form a donor molecule-containing fragment and an acceptor molecule-containing fragment. The donor molecule-containing fragment comprising the tagging portion is hybridized with the CO comprising a nucleotide sequence hybridizable with the tagging portion of the 5'-tagged PO but the acceptor molecule-containing fragment does not involve in hybridization with the CO, thus failing to provide the signal from the acceptor.

In the event that the target nucleic acid sequence is absent, the uncleaved 5'-tagged PO is hybridized with the CO and the interaction between the donor molecule and the acceptor molecule occurs, thereby providing the signal from the acceptor molecule.

In the presence of the target nucleic acid sequence, the uncleaved PO/CO duplex is not formed due to cleavage of the 5'-tagged PO and thus fails to provide the signal from the acceptor. The measurement of extinction (or reduction) of the single from the acceptor molecule on the solid substrate enables to determine the presence of the target nucleic acid sequence.

According to a preferred embodiment, the donor molecule and the acceptor molecule on the 5'-tagged PO are adjacent to each other to the extent that energy is passed between them. The donor molecule and the acceptor molecule are located to the 5'-tagged PO in a 5' to 3' direction or 3' to 5' direction.

According to a preferred embodiment, both the donor molecule and the acceptor molecule are located on the targeting portion of the 5'-tagged PO or one of them is located on the targeting portion and the other located on the tagging portion of the 5'-tagged PO.

The second measurement fashion is illustrated in FIGS. 10-12.

FIG. 10 using the non-tagged PO represents an embodiment to measure signal from the donor molecule. According to a preferred embodiment, the nucleotide sequence hybridizable with the PO in the CO comprises a nucleotide sequence hybridizable with the targeting portion of the PO. The hybridization reaction in the is step (c) is performed under conditions such that the donor-containing fragment is not hybridized with the CO; wherein the interactive dual label is located to the extent that a signal from the donor molecule is unquenched by the acceptor molecule when the uncleaved PO/CO duplex is formed and the step (d) is performed by detecting a signal from the donor molecule.

As exemplified in FIG. 10, where the donor molecule and the acceptor molecule are conformationally adjacent to each other on the non-tagged PO to the extent that energy is passed between the donor molecule and the acceptor molecule, the non-tagged PO hybridized with the target nucleic acid sequence is cleaved to form a donor molecule-containing fragment and an acceptor molecule-containing fragment. The hybridization is carried out in the step (c) under conditions that the donor molecule-containing fragment is not hybridized with the CO. Therefore, the signal from the donor molecule is not provided on the solid substrate.

In the event that the target nucleic acid sequence is absent, the uncleaved non-tagged PO is hybridized with the CO to separate the donor molecule and the acceptor molecule, resulting in prevention of interaction between the donor molecule and the acceptor molecule. Illumination of light with excitation wavelength for the donor molecule (e.g., a reporter molecule) generates fluorescence from the donor molecule that is not quenched by the acceptor molecule, finally providing a fluorescent signal from the donor.

In the presence of the target nucleic acid sequence, the uncleaved PO/CO duplex is not formed due to cleavage of the PO and the donor-containing fragment is not hybridized with the CO, thus failing to provide the signal from the donor. The measurement of extinction (or reduction) of the single from the donor molecule on the solid substrate enables to determine the presence of the target nucleic acid sequence.

According to a preferred embodiment, the donor molecule and the acceptor molecule are located to the non-tagged PO in a 5' to 3' direction or 3' to 5' direction, more preferably in a 5' to 3' direction.

FIGS. 11 and 12 using the tagged PO represent embodiments to measure signal from the donor molecule. According to a preferred embodiment, the PO is a 3'-tagged PO further comprising in its 3'-portion a tagging portion having a nucleotide sequence non-complementary to the target nucleic acid sequence or a 5'-tagged PO further comprising in its 5'-portion a tagging portion having a nucleotide sequence non-complementary to the target nucleic acid sequence and the nucleotide sequence hybridizable with the PO in the CO comprises a nucleotide sequence hybridizable with the tagging portion of the PO. The donor-containing fragment comprises the tagging portion hybridizable with the CO and in the hybridization reaction in the step (c), the donor-containing fragment is hybridized with the CO. The interactive dual label is preferably located to the extent that a signal from the donor molecule is quenched by the acceptor molecule when the uncleaved PO/CO duplex is formed, wherein the step (d) is performed by detecting a signal from the donor molecule.

As illustrated in FIG. 11 using the 3'-tagged PO, where the donor molecule and the acceptor molecule are conformationally adjacent to each other to the extent that energy is passed between the donor molecule and the acceptor molecule, the 3'-tagged PO hybridized with the target nucleic acid sequence is cleaved to form a donor molecule-containing fragment and an acceptor molecule-containing fragment. The donor molecule-containing fragment comprising the tagging portion is hybridized with the CO comprising a nucleotide sequence hybridizable with the tagging portion of the 3'-tagged PO but the acceptor molecule-containing fragment does not involve in hybridization with the CO, thus providing the signal from the donor.

In the event that the target nucleic acid sequence is absent, the uncleaved 3'-tagged PO is hybridized with the CO and the interaction between the donor molecule and the acceptor molecule occurs to cause passage of energy of the donor molecule to the acceptor molecule, thereby generating no fluorescence from the donor molecule.

In the presence of the target nucleic acid sequence, the 3'-tagged PO is cleaved and the donor molecule-containing fragment comprising the tagging portion is hybridized with the CO, providing the signal from the donor molecule. The measurement of generation (or increase) of the single from the donor molecule on the solid substrate enables to determine the presence of the target nucleic acid sequence.

According to a preferred embodiment, the donor molecule and the acceptor molecule on the 3'-tagged PO are adjacent to each other to the extent that energy is passed between them. The acceptor molecule and the donor molecule are located to the 3'-tagged PO in a 5' to 3' direction.

According to a preferred embodiment, both the acceptor molecule and the donor molecule are located on the targeting portion of the 3'-tagged PO, or the acceptor molecule is located on the targeting portion and the donor molecule located on the tagging portion of the 3'-tagged P0.

As illustrated in FIG. 12 using the 5'-tagged PO, where the donor molecule and the acceptor molecule are conformationally adjacent to each other to the extent that energy is passed between the donor molecule and the acceptor molecule, the 5'-tagged PO hybridized with the target nucleic acid sequence is cleaved to form an acceptor molecule-containing fragment and a donor molecule-containing fragment comprising the tagging portion. The donor molecule-containing fragment comprising the tagging portion is hybridized with the CO comprising a nucleotide sequence hybridizable with the tagging portion of the 5'-tagged PO but the acceptor molecule-containing fragment does not involve in hybridization with the CO, thus providing the signal from the donor indicative of the presence of the target nucleic acid sequence. In the event that the target nucleic acid sequence is absent, the uncleaved 5'-tagged PO is hybridized with the CO and the interaction between the donor molecule and the acceptor molecule occurs to cause passage of energy of the donor molecule to the acceptor molecule, thereby generating no fluorescence from the donor molecule.

In the presence of the target nucleic acid sequence, the 5'-tagged PO is cleaved and the donor molecule-containing fragment comprising the tagging portion is hybridized with the CO, providing the signal from the donor molecule. The measurement of generation (or increase) of the single from the donor molecule on the solid substrate enables to determine the presence of the target nucleic acid sequence.

According to a preferred embodiment, the donor molecule and the acceptor molecule on the 5'-tagged PO are adjacent to each other to the extent that energy is passed between them. The donor molecule and the acceptor molecule are located to the 5'-tagged PO in a 5' to 3' direction.

According to a preferred embodiment, both the donor molecule and the acceptor molecule are located on the targeting portion of the 5'-tagged PO, or the acceptor molecule is located on the targeting portion and the donor molecule located on the tagging portion of the 5'-tagged PO.

In the alternative using the tagged PO, the CO comprises a nucleotide sequence hybridizable with a part (or all) of the tagging portion and a part (or all) of the targeting portion of the tagged PO. The position of the interactive dual label on the PO is determined in considering cleavage method and cleavage site as well as the sequence of the CO.

III. Target Detection Process by POCH Using Intercalation Agent

The present invention also exhibits excellent performance using an intercalating agent in detection of the target nucleic acid sequence.

In another aspect of this invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with an upstream oligonucleotide and a probing oligonucleotide (PO); wherein the upstream oligonucleotide comprises a hybridizing nucleotide sequence complementary to the target nucleic acid sequence; the PO comprises a targeting portion comprising a hybridizing nucleotide sequence complementary to the target nucleic acid sequence; the upstream oligonucleotide is located upstream of the PO; the upstream oligonucleotide or its extended strand induces cleavage of the PO by an enzyme having a 5' nuclease activity;

(b) contacting the resultant of the step (a) to the enzyme having the 5' nuclease activity under conditions for cleavage of the PO; wherein when the PO is hybridized with the target nucleic acid sequence, the PO is cleaved by the enzyme having the 5' nuclease activity to produce a cleaved fragment;

(c) performing a hybridization reaction in the presence of an intercalating agent by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the cleaved fragment is not hybridized with the CO and an uncleaved PO is hybridized with the CO to form an uncleaved PO/CO duplex; and (d) detecting occurrence of the cleavage of the PO by measuring a signal from the intercalating agent on the solid substrate; whereby the occurrence of the PO cleavage indicates the presence of the target nucleic acid sequence.

Since the third embodiment of this invention is the same as the first embodiment using the single label except for a label system, the common descriptions between them are omitted in order to avoid undue redundancy leading to the complexity of this specification.

According to a preferred embodiment, the hybridization reaction is performed under conditions such that the cleaved fragment produced by cleavage of the PO is not hybridized with the CO.

Exemplified intercalating dyes useful in this invention include SYBR™ Green I, PO-PRO™-1, BO-PRO™-1, SYTO™ 43, SYTO™ 44, SYTO™ 45, SYTOX™ Blue, POPO™-1, POPO™-3, BOBO™-1, BOBO™-3, LO-PRO™-1, JO-PRO™-1, YO-PRO™ 1, TO-PRO™ 1, SYTO™ 11, SYTO™ 13, SYTO™ 15, SYTO™ 16, SYTO™ 20, SYTO™ 23, TOTO™-3, YOYO™ 3, GelStar™ and thiazole orange. The intercalating dyes intercalate specifically into double-stranded nucleic acid molecules to generate signals.

Where the target nucleic acid sequence is present, the uncleaved PO/CO duplex is not formed due to cleavage of the PO and therefore the signal from the intercalating agent is not provided. The measurement of extinction (or reduction) of the single from the intercalating agent on the solid substrate enables to determine the presence of the target nucleic acid sequence (see FIG. 13).

According to a preferred embodiment, the method further comprises repeating the steps (a)-(b), (a)-(c) or (a)-(d) with denaturation between repeating cycles. This repetition permits to amplify the target nucleic acid sequence and/or the target-signal.

According to a preferred embodiment, the steps (a)-(d) are performed in a reaction vessel or in separate reaction vessels. More preferably, the steps (a)-(b) and steps (c)-(d) are performed in a reaction vessel or in separate reaction vessels.

Preferably, the steps (a)-(b) and steps (c)-(d) may be separately performed even in a reaction vessel. For example, where the hybridization between the targeting portion of the PO and the target nucleic acid sequence occurs under higher stringent conditions than those for hybridization between the fragment from the PO and the CO, the repetition of the steps (a)-(b) may be carried out with no proceeding with the steps (c)-(d). After termination of the repetition of the steps (a)-(b), the steps (c)-(d) may be successively carried out.

Where the steps (a)-(b) and steps (c)-(d) may be separately performed, the steps (a)-(b) is repeatedly carried out with denaturation between repeating cycles.

Where the present invention using an upstream primer is carried out by repeating steps with denaturation between repeating cycles, it is preferable to perform the method in the presence of a downstream primer. Most preferably, the present method is carried out in accordance with PCR (polymerase chain reaction).

Where the present invention using an upstream probe is carried out by repeating steps with denaturation between repeating cycles, it is preferable to perform the method in the presence of a downstream primer.

The present invention does not require that target nucleic acid sequences to be is detected and/or amplified have any particular sequence or length, including any DNA (gDNA and cDNA) and RNA molecules.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp: 120-122 (1992), U.S. Pat. No. 5,665,539, Niemeyer et al., Trends in Biotechnology 23 pp: 208-216 (2005), U.S. Pat. Pub. No. 2005/0239108 and Ye et al., Journal of Environmental Science 22 pp: 796-800 (2010)).

The term "nucleotide variation" used herein refers to any single or multiple nucleotide substitutions, deletions or insertions in a DNA sequence at a particular location among contiguous DNA segments that are otherwise similar in sequence.

Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation.

Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a DNA molecule. In other words, the term nucleotide variation includes a wild type and its any mutant type at a particular location in a DNA molecule.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to a preferred embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no cleavage of the PTO.

Alternatively, it is possible to use PO cleavage depending on the hybridization of PO having a complementary sequence to a nucleotide variation in a target nucleic acid sequence. For example, under controlled conditions, a PO having a complementary sequence to the nucleotide variation in the target nucleic acid sequence is hybridized with the matching template and then cleaved. While, under the controlled conditions, the PO is not hybridized with a mismatching template having non-complementary sequence in the nucleotide variation position and not cleaved. Preferably, in this case, the complementary sequence to the nucleotide variation in the PO is positioned at its middle of the 3'-targeting portion of the PO.

Alternatively, the present invention uses the PO having the nucleotide variation discrimination site positioned on the 5'-end part of the 3'-targeting portion for selectivity of the PO to a specific nucleotide variation. The 5'-end part of the 3'-targeting portion of the PO is positioned to a nucleotide variation in a target nucleic acid sequence for the detection of the nucleotide variation and the 5'-end part of the 3'-targeting portion of the PO has a complementary sequence to the nucleotide variation in a target nucleic acid sequence.

The term used herein "nucleotide variation discrimination site" with reference to the PO means a site (i) comprising a complementary sequence to the nucleotide variation on the target nucleic acid and (ii) positioned on a 5'-end part of the 3'-targeting portion.

Where the PO is hybridized with the target nucleic acid sequence (i.e., match template) having the nucleotide variation complementary to the nucleotide variation discrimination site, the 5'-end part of the 3'-targeting portion forms a double strand with the match template; however, where the PO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

It is noteworthy that such distinct hybridization patterns on the nucleotide variation of interest are responsible for differences in initial cleavage sites of the PO.

The 5' nuclease used in the present invention is an enzyme capable of digesting one strand of a double-stranded nucleic acid molecule in a 5' to 3' direction exonucleolytically or endonucleolytically. Generally, the cleavage site on the PO by the 5' nuclease may be varied depending on hybridization of the 5'-end portion of the PO.

Where the PO is hybridized with the target nucleic acid sequence (i.e., match template) having the nucleotide variation complementary to the variation discrimination site, the 5'-end part of the 3'-targeting portion forms a double strand with the target nucleic acid sequence to induce cleavage from a first initial cleavage site.

Where the PO is hybridized with a target nucleic acid sequence (i.e., mismatch template) having a nucleotide variation non-complementary to the variation discrimination site, the 5'-end part of the 3'-targeting portion does not form a double strand with the target nucleic acid sequence to induce cleavage from a second initial cleavage site located downstream of the first initial cleavage site.

It is noteworthy that the second initial cleavage site is located downstream of the first initial cleavage site.

The term used herein "a first initial cleavage site" in conjunction with the PO means to a cleavage site of the PO being firstly cleaved when the PO is hybridized with the target nucleic acid sequence having the nucleotide variation complementary to the variation discrimination site. The term used herein "a second initial cleavage site" in conjunction with the PO means to a cleavage site of the PO being firstly cleaved when the PO is hybridized with a target nucleic acid sequence having a nucleotide variation non-complementary to the variation discrimination site.

According to a preferred embodiment, the nucleotide variation discrimination site is located within 10 nucleotides, more preferably 8 nucleotides, still more preferably 6 nucleotides, still much more preferably 4 nucleotides, 3 nucleotides, 2 nucleotides or 1 nucleotide apart from the 5'-end of the 3'-targeting portion of the PO. Preferably, the nucleotide variation discrimination site is located at the 5'-end of the 3'-targeting portion of the PO.

The term "site" with reference to either nucleotide variation discrimination site of probes or nucleotide variation site on target sequences is used herein to encompass not only a single nucleotide but also a plurality of nucleotides.

The PO having the nucleotide variation discrimination site positioned on the 5'-end part of the 3'-targeting portion may be employed to detect a nucleotide variation together with a blocker resistant to cleavage by the enzyme having 5' nuclease activity.

For example, PO has a blocker portion containing, as a blocker, at least one nucleotide resistant to cleavage by the enzyme having 5' nuclease activity and the blocker portion is positioned at a site to be initially cleaved upon hybridization of the PO with the mismatch template. Where the PO having the blocker portion is hybridized with a match template, the cleavage from a first initial cleavage site is not affected. However, where the PO having the blocker portion is hybridized with a mismatch template, the blocker portion prevents the cleavage from a second initial cleavage site.

The number of blockers contained in the blocker portion may be not limited, preferably, 1-10, more preferably 2-10, still more preferably 3-8, most preferably 3-6 blockers. The blockers present in the probes may be in a continuous or intermittent manner, preferably a continuous manner. The nucleotides as blockers with a backbone resistant to the 5' to 3' exonuclease activity include any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

Optionally, the detection of nucleotide variations may be accomplished by an appropriate selection of label location in considering the locations of the first initial cleavage site and the second initial cleavage site with no use of blockers.

Where a single label is used, the suitable locations of the single label enable the followings: a single label-containing fragment formed by cleavage of the PO hybridized with the match template is not hybridized with the CO but a single label-containing fragment formed by cleavage of the PO hybridized with the mismatch template is hybridized with the CO. The hybridization between the CO and the single label-containing fragment formed by cleavage of the PO hybridized with the mismatch template provides signal identical to that provided by hybridization between the uncleaved PO and the CO, thereby permitting to detect nucleotide variations.

According to a more preferred embodiment, a single label linked to the PO is located on a nucleotide between the first initial cleavage site and the second initial cleavage site.

In case that an interactive dual label is used, the suitable locations of the dual label enable the followings: (i) upon cleaving the PO hybridized with the match template, the dual label is separated from each other and at least one of a donor-containing fragment and an acceptor-containing fragment is not hybridized with the CO. (ii) upon cleaving the PO hybridized with the mismatch template, the dual label is not separated from each other and a dual label-containing fragment is hybridized with the CO. The hybridization between the CO and the dual label-containing fragment formed by cleavage of the PO hybridized with the mismatch template provides signal identical to that provided by hybridization between the uncleaved PO and the CO, thereby permitting to detect nucleotide variations.

According to a more preferred embodiment, where the PO with a dual label is used, one of the dual label is linked to a nucleotide present upstream of the first initial cleavage site and the other to a nucleotide present between the first initial cleavage site and the second initial cleavage site.

For example, where the 5'-tagged PO having the nucleotide variation discrimination site positioned on the 5'-end part of the 3'-targeting portion together with the CO to be hybridized with the 5'-tagging portion are employed, a suitable location of labels permits to nucleotide variations with no use of blockers.

Where the 5'-tagged PO with a single label is used, the single label linked to the 5'-tagged PO is preferably located on a nucleotide between the first initial cleavage site and the second initial cleavage site.

Figure 21:
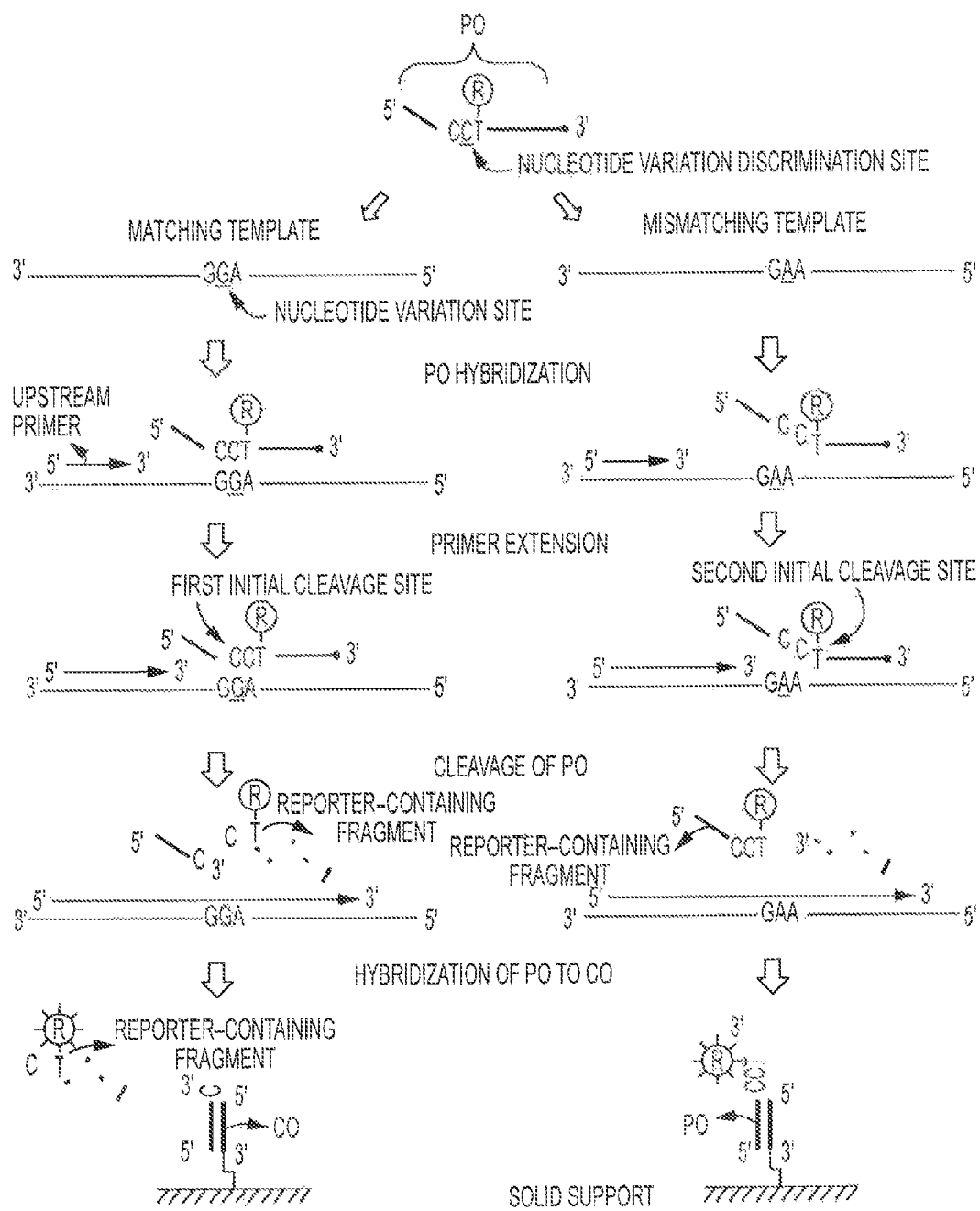
FIG. 21 schematically represents the POCH assay using a 5'-tagged PO for detecting a single nucleotide variation.

FIG. 21 represents embodiments to detect nucleotide variation using 5'-tagged PO with a single label. The nucleotide variation discrimination site is positioned at 1 nucleotide apart from the 5'-end of the 5'-end part of the 3'-targeting portion. The single label is linked to the nucleotide positioned between the first initial cleavage site and the second initial cleavage site.

When the 5'-tagged PO containing the single label is hybridized with the match template, it is cleaved at the first initial cleavage site and a 5'-tagging portion-containing fragment without the single label is generated. As the CO comprises a nucleotide sequence hybridizable with the tagging portion of the PO, the single label-containing fragment formed by cleavage of the PO hybridized with the match template is not hybridized with the CO. When the 5'-tagged PO containing the single label is hybridized with the mismatch template, it is cleaved at the second initial cleavage site and a 5'-tagging portion-containing fragment with the single label is generated. As the CO comprises a nucleotide sequence hybridizable with the tagging portion of the PO, the single label-containing fragment formed by cleavage of the PO hybridized with the mismatch template is hybridized with the CO. The hybridization between the CO and the single label-containing fragment formed by cleavage of the PO hybridized with the mismatch template provides signal identical to that provided by hybridization between the uncleaved PO and the CO.

Consequently, different signals may be provided depending on the presence of nucleotide variations.

Where the 5'-tagged PO with a dual label is used, it is preferred that one of the dual label is linked to a nucleotide present upstream of the first initial cleavage site (for example, 5'-end of the 5-tagging portion of PO) and the other to a nucleotide present between the first initial cleavage site and the second initial cleavage site.

When the 5'-tagged PO containing the dual label is hybridized with the match template, it is cleaved at the first initial cleavage site and the dual label is separated to form a donor molecule-containing fragment and an acceptor molecule-containing fragment. One of the fragments comprises the 5'-tagging portion and it is hybridized with the CO comprising a nucleotide sequence hybridizable with the tagging portion of the 5'-tagged PO. When the 5'-tagged PO containing the dual label is hybridized with the mismatch template, it is cleaved at the second initial cleavage site, generating a 5'-tagging portion-containing fragment with the dual label. The 5'-tagging portion-containing fragment with the dual label is hybridized with the CO and the hybridization product provides the identical signal to that from the hybridization between the uncleaved 5'-tagged PO and the CO.

Consequently, different signals may be provided depending on the presence of nucleotide variations.

Figure 22:
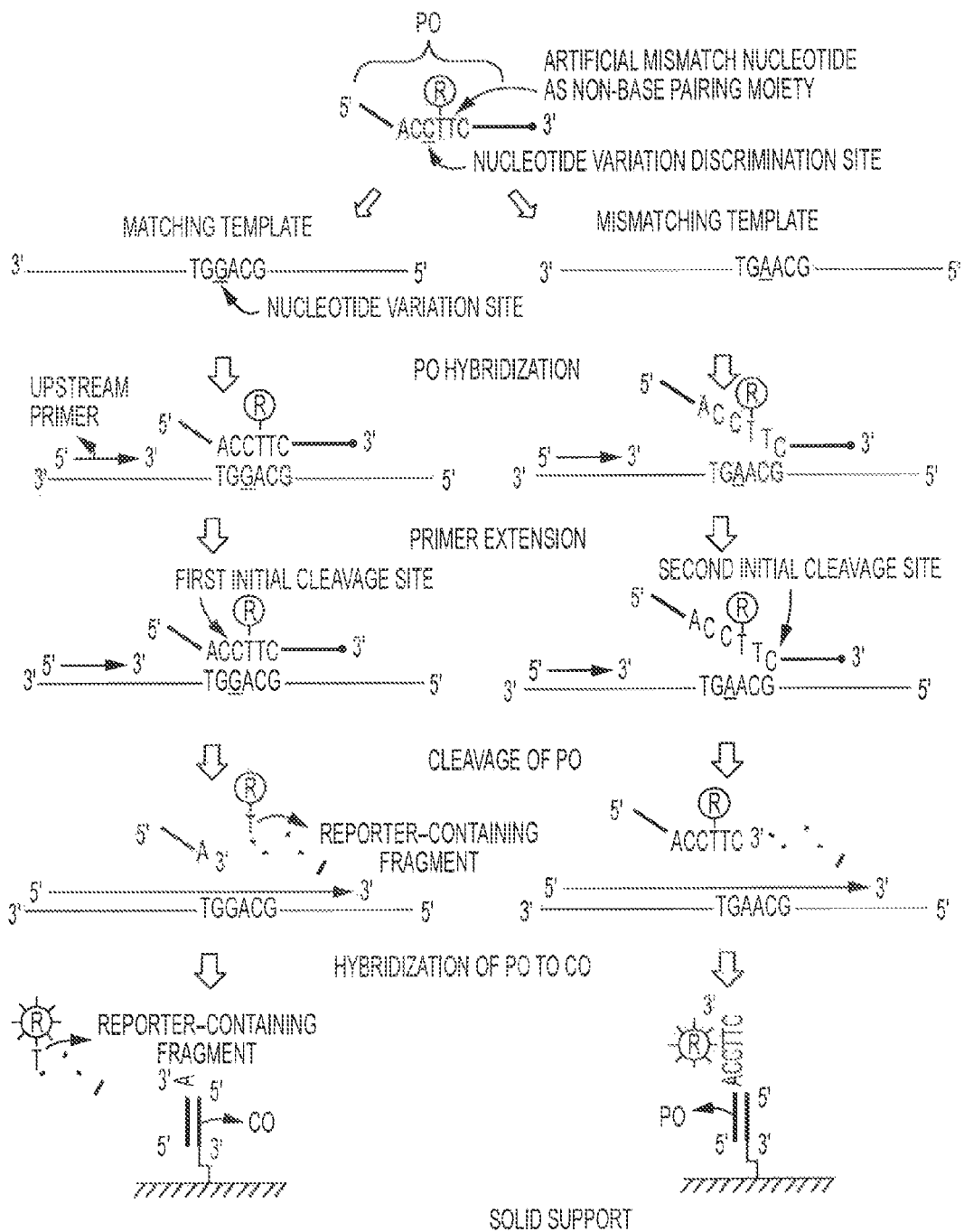
FIG. 22 schematically represents the POCH assay using a 5'-tagged PO having an artificial mismatch nucleotide as non-base pairing moiety for detecting a single nucleotide variation.

According to a preferred embodiment, it is preferable that the 5'-end part of the 3'-targeting portion of the PO comprises a non-base pairing moiety located within 1-10 nucleotides (more preferably 1-5 nucleotides) apart from the nucleotide variation discrimination site FIG. 22 represents embodiments to detect nucleotide variation using the non-base pairing moiety.

The non-base pairing moiety prevents the 5'-end part of the 3'-targeting portion from formation of a double strand with the target nucleotide sequence when the PO is hybridized with the target nucleic acid sequence having the nucleotide variation non-complementary to the variation discrimination site.

The use of the non-base pairing moiety (e.g., mismatch nucleotide) enhances discrimination potential of the PO to nucleotide variations.

According to a preferred embodiment, the non-base pairing moiety does not inhibit the formation of a double strand between the 5'-end part and the target nucleic acid sequence when the PO is hybridized with the target nucleic acid sequence having the nucleotide variation complementary to the nucleotide variation discrimination site.

According to a preferred embodiment, the non-base pairing moiety widens the distance between the first initial cleavage site on the hybrid of the PO and the matching template and the second initial cleavage site on the hybrid of the PO and the mismatching template.

The non-base pairing moiety includes any moieties not forming a base pair between target nucleic acid sequences. Preferably, the non-base pairing moiety is (i) a nucleotide comprising an artificial mismatch base, a non-base pairing base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PO.

The non-base pairing moiety introduced into the 5'-end part has preferably 1-10, more preferably 1-5, still more preferably 1-2 moieties. A plurality of non-base pairing moieties in the 5'-end part may be present in a consecutive or intermittent manner. Preferably, the non-base pairing moiety has 2-5 consecutive moieties.

Preferably, the non-base pairing moiety is a non-base pairing chemical compound.

According to a preferred embodiment, the nucleotide variation discrimination site and the non-base pairing moiety of the PO are located within 10 nucleotides (more preferably 8 nucleotides, 7 nucleotides, 6 nucleotides, 5 nucleotides, 4 nucleotides, 3 nucleotides, 2 nucleotides or 1 nucleotide, still more preferably 1 nucleotide) apart from the 5'-end of the 3'-targeting portion.

According to a preferred embodiment, the non-base pairing moiety is located downstream of the first initial cleavage site.

According to a preferred embodiment, the target nucleic acid sequence used in the present invention is a pre-amplified nucleic acid sequence by an amplification primer.

The advantages of the present invention may be highlighted in the simultaneous (multiplex) detection of at least two target nucleic acid sequences. According to a preferred embodiment, the method is performed to detect at least two types (more preferably, at least three types, still more preferably at least five types) of target nucleic acid sequences. The upstream oligonucleotide comprises at least two types (more preferably, at least three types, still more preferably at least five types) of oligonucleotides, the PO comprises at least two types (more preferably at least three types, still more preferably at least five types) of the POs and the CO comprises at least two types (more preferably, at least three types, still more preferably at least five types) of the CO.

In the embodiment using the tagged PO, the tagging portions of the at least two POs may have the identical sequence to or different sequence from each other. For instance, where the present invention is carried out for screening target nucleic acid sequences (e.g. detection of a nucleic acid sequence among a plurality of target nucleic acid sequences), the POs having the tagging portions with the identical sequence may be used.

Furthermore, a single type of the CO may be used for detection of a plurality of target nucleic acid sequences. For example, where the POs having an identical sequence in their tagging portions are employed for screening target nucleic acid sequences, a single type of the CO may be used.

According to a preferred embodiment, the present method may be performed using at least two downstream primers.

Preferable Embodiments of the Invention

In a preferable embodiment of this invention, there is provided a method for detecting a target nucleic acid sequences from a DNA or a mixture of nucleic acids by a POCH (PO Cleavage and Hybridization) assay on a solid substrate, comprising:

(a) hybridizing the target nucleic acid sequences with a primer pair comprising an upstream primer and a downstream primer and a PO (Probing Oligonucleotide); wherein each of the upstream primer and the downstream primer comprise a hybridizing nucleotide sequence complementary to the target nucleic acid sequence; the PO comprises a targeting portion comprising a hybridizing nucleotide sequence complementary to the target nucleic acid sequence; the PO has a single label; the PO is blocked at its 3'-end to prohibit its extension; the targeting portion of the PO is located between the upstream primer and the downstream primer; an extended strand of the upstream primer induces cleavage of the PO by a template-dependent nucleic acid polymerase having a 5' nuclease activity;

(b) contacting the resultant of the step (a) to a template-dependent nucleic acid polymerase having a 5' nuclease activity under conditions for extension of the primers and for cleavage of the PO; wherein when the PO is hybridized with the target nucleic acid sequences, the PO is cleaved by the template-dependent nucleic acid polymerase having the 5' nuclease activity to produce a single label-containing fragment;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex;

(d) denaturing the resultant of the step (c);

(e) repeating the steps (a)-(d) at least twice; and (f) detecting occurrence of the cleavage of the PO by measuring a signal from the single label on the solid substrate; whereby the occurrence of the PO cleavage indicates the presence of the target nucleic acid sequence.

Alternatively, the step (b) is followed by (b-1) denaturing the resultant of the step (b) and (b-2) repeating the steps (a)-(b-1) at least twice. In this case, the steps (d) and (e) are optional.

The measurement of the signal from the single label may be performed for each cycle of the repetition, after the repetition of step (d) or at predetermined time-intervals during the repetition of step (d).

In another preferable embodiment of this invention, there is provided a method for detecting a target nucleic acid sequences from a DNA or a mixture of nucleic acids by a POCH (PO Cleavage and Hybridization) assay on a solid substrate, comprising:

(a) hybridizing the target nucleic acid sequences with a primer pair comprising an upstream primer and a downstream primer and a PO (Probing Oligonucleotide); wherein each of the upstream primer and the downstream primer comprise a hybridizing nucleotide sequence complementary to the target nucleic acid sequence; the PO comprises a targeting portion comprising a hybridizing nucleotide sequence complementary to the target nucleic acid sequence; the PO has an interactive dual label comprising a donor molecule and an acceptor molecule; the PO is blocked at its 3'-end to prohibit its extension; the targeting portion of the PO is located between the upstream primer and the downstream primer; an extended strand of the upstream primer induces cleavage of the PO by a template-dependent nucleic acid polymerase having a 5' nuclease activity;

(b) contacting the resultant of the step (a) to a template-dependent nucleic acid polymerase having a 5' nuclease activity under conditions for extension of the primers and for cleavage of the PO; wherein when the PO is hybridized with the target nucleic acid sequences, the PO is cleaved by the enzyme having the 5' nuclease activity to separate the interactive dual label, whereby a donor-containing fragment and an acceptor-containing fragment are produced;

(c) performing a hybridization reaction by contacting the resultant of the step (b) to a capturing oligonucleotide (CO) immobilized onto the solid substrate; wherein the hybridization reaction is performed under conditions such that at least one of the donor-containing fragment and the acceptor-containing fragment is not hybridized with the CO and an uncleaved PO is hybridized with the CO to form an uncleaved PO/CO duplex; wherein a signal from the uncleaved PO/CO duplex is differentiated from a signal provided at the time that at least one of the donor-containing fragment and the acceptor-containing fragment is not hybridized with the CO;

(d) denaturing the resultant of the step (c);

(e) repeating the steps (a)-(d) at least twice; and (f) detecting occurrence of the cleavage of the PO by measuring a signal from the interactive dual label on the solid substrate; whereby the occurrence of the PO cleavage indicates the presence of the target nucleic acid sequence.

Alternatively, the step (b) is followed by (b-1) denaturing the resultant of the step (b) and (b-2) repeating the steps (a)-(b-1) at least twice. In this case, the steps (d) and (e) are optional.

In still another preferable embodiment of this invention, there is provided a method for detecting a target nucleic acid sequences from a DNA or a mixture of nucleic acids by a POCH (PO Cleavage and Hybridization) assay on a solid substrate, comprising:

(a) hybridizing the target nucleic acid sequences with a primer pair comprising an upstream primer and a downstream primer and a PO (Probing Oligonucleotide); wherein each of the upstream primer and the downstream primer comprise a hybridizing nucleotide sequence complementary to the target nucleic acid sequence; the PO comprises a targeting portion comprising a hybridizing nucleotide sequence complementary to the target nucleic acid sequence; the PO is blocked at its 3'-end to prohibit its extension; the targeting portion of the PO is located between the upstream primer and the downstream primer; an extended strand of the upstream primer induces cleavage of the PO by a template-dependent nucleic acid polymerase having a 5' nuclease activity;

(b) contacting the resultant of the step (a) to a template-dependent nucleic acid polymerase having a 5' nuclease activity under conditions for extension of the primers and for cleavage of the PO; wherein when the PO is hybridized with the target nucleic acid sequences, the PO is cleaved by the template-dependent nucleic acid polymerase having the 5' nuclease activity to produce a single label-containing fragment;

(c) performing a hybridization reaction in the presence of an intercalating agent by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex;

(d) denaturing the resultant of the step (c);

(e) repeating the steps (a)-(d) at least twice; and (f) detecting occurrence of the cleavage of the PO by measuring a signal from the intercalating agent on the solid substrate; whereby the occurrence of the PO cleavage indicates the presence of the target nucleic acid sequence.

Alternatively, the step (b) is followed by (b-1) denaturing the resultant of the step (b) and (b-2) repeating the steps (a)-(b-1) at least twice. In this case, the steps (d) and (e) are optional.

IV. Target Detection Process by POCH Assay Based on Upstream Oligonucleotide-Independent 5' Nuclease Activity.

In a further aspect of the present invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with a probing oligonucleotide (PO); wherein the PO comprises a targeting portion comprising a hybridizing nucleotide sequence complementary to the target nucleic acid sequence; the PO has a single label;

(b) contacting the resultant of the step (a) to an enzyme having a 5' nuclease activity under conditions for cleavage of the PO; wherein when the PO is hybridized with the target nucleic acid sequence, the PO is cleaved by the enzyme having the 5' nuclease activity to produce a single label-containing fragment;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex; and (d) detecting occurrence of the cleavage of the PO by measuring a signal from the single label on the solid substrate; whereby the occurrence of the PO cleavage indicates the presence of the target nucleic acid sequence.

In a still further aspect of this invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with a probing oligonucleotide (PO); wherein the PO comprises a targeting portion comprising a hybridizing nucleotide sequence complementary to the target nucleic acid sequence; the PO has an interactive dual label comprising a donor molecule and an acceptor molecule;

(b) contacting the resultant of the step (a) to an enzyme having a 5' nuclease activity under conditions for cleavage of the PO; wherein when the PO is hybridized with the target nucleic acid sequence, the PO is cleaved by the enzyme having the 5' nuclease activity to separate the interactive dual label, whereby a donor-containing fragment and an acceptor-containing fragment are produced;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that at least one of the donor-containing fragment and the acceptor-containing fragment is not hybridized with the CO and an uncleaved PO is hybridized with the CO to form an uncleaved PO/CO duplex; wherein a signal from the uncleaved PO/CO duplex is differentiated from a signal provided at the time that at least one of the donor-containing fragment and the acceptor-containing fragment is not hybridized with the CO; and (d) detecting occurrence of the cleavage of the PO by measuring a signal from the interactive dual label on the solid substrate; whereby the occurrence of the PO cleavage indicates the presence of the target nucleic acid sequence.

In a still further aspect of this invention, there is provided a method for detecting a target nucleic acid sequence from a DNA or a mixture of nucleic acids by a POCH (PO Cleavage and Hybridization) assay on a solid substrate, comprising:

(a) hybridizing the target nucleic acid sequence with a probing oligonucleotide (PO); wherein the PO comprises a targeting portion comprising a hybridizing nucleotide sequence complementary to the target nucleic acid sequence;

(b) contacting the resultant of the step (a) to an enzyme having a 5' nuclease activity under conditions for cleavage of the PO; wherein when the PO is hybridized with the target nucleic acid sequence, the PO is cleaved by the enzyme having the 5' nuclease activity to produce a cleaved fragment;

(c) performing a hybridization reaction in the presence of an intercalating agent by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the cleaved fragment is not hybridized with the CO and an uncleaved PO is hybridized with the CO to form an uncleaved PO/CO duplex; and (d) detecting occurrence of the cleavage of the PO by measuring a signal from the intercalating agent on the solid substrate; whereby the occurrence of the PO cleavage indicates the presence of the target nucleic acid sequence.

The present invention may be carried out with no use of the upstream oligonucleotide. The PO may be cleaved by upstream oligonucleotide-independent 5' nuclease activity. In such case, conventional enzymes having upstream oligonucleotide-independent 5' nuclease activity may be used.

For example, 5'-FEN nuclease having upstream oligonucleotide-independent 5'-exonuclease activity and/or 5'-endonuclease activity may be used.

Among template-dependent polymerases, there are several enzymes having upstream oligonucleotide-independent 5' nuclease activity (5' exonuclease activity and/or 5' endonuclease activity), e.g., Taq DNA polymerase (see, lawyer et al, *Genome Res.* 2 pp: 275-287 (1993), WO 2008/011004 and Lyamichev et. al., Science 260 pp: 778-783 (1993)).

According to a preferred embodiment, the cleavage of the PO by the template-dependent polymerase having an upstream oligonucleotide-independent 5' nuclease activity is affected by position of labels or linking type of labels present in the PO. Preferably, where a label is linked to the 5'-end of the non-tagged PO, the cleavage of the non-tagged PO by the template-dependent polymerase having a 5' nuclease activity may be more efficient if the label is linked to a phosphate group of the 5'-end of the non-tagged PO, particularly through a carbon-spacer. Where the label is linked to a base of the 5'-end of the non-tagged PO or the carbon-spacer is not used, the cleavage of the non-tagged PO is unlikely to occur.

The cleavage efficiency for the upstream oligonucleotide-dependent 5' nuclease activity may be higher than that for the upstream oligonucleotide-independent 5' nuclease activity.

The upstream oligonucleotide-independent 5' nuclease activity is more susceptible to reaction conditions (e.g., types of enzymes, buffer compositions and sequences of the PO).

Considering amplification of target nucleic acid sequences and cleavage efficiency of the PO, the POCH assay of the present invention is preferably performed using upstream oligonucleotides.

Kits for Target Detection

In further aspect of this invention, there is provided a kit for detecting a target nucleic acid sequence from a DNA or a mixture of nucleic acids by a POCH (PO Cleavage and Hybridization) assay on a solid substrate, comprising:

(a) a probing oligonucleotide (PO) comprising a targeting portion comprising a hybridizing nucleotide sequence complementary to the target nucleic acid sequence;

(b) an upstream oligonucleotide comprising a hybridizing nucleotide sequence complementary to the target nucleic acid sequence; wherein the upstream oligonucleotide is located upstream of the PO; the upstream oligonucleotide or its extended strand induces cleavage of the PO by an enzyme having a 5' nuclease activity; and (c) a capturing oligonucleotide (CO) immobilized onto the solid substrate; wherein the CO comprises a nucleotide sequence hybridizable with the PO, whereby an PO uncleaved by the enzyme having the 5' nuclease activity is hybridized with the CO to form an uncleaved PO/CO duplex.

Since the kit of this invention is constructed to perform the detection method of the present invention described above, the common descriptions between them are omitted in order to avoid undue redundancy leading to the complexity of this specification.

According to a preferred embodiment, the PO has a single label or an interactive dual label.

According to a preferred embodiment, the PO is a 3'-tagged PO further comprising in its 3'-portion a tagging portion having a nucleotide sequence non-complementary to the target nucleic acid sequence or a 5'-tagged PO further comprising in its 5'-portion a tagging portion having a nucleotide sequence non-complementary to the target nucleic acid sequence, and the nucleotide sequence hybridizable with the PO in the CO comprises a nucleotide sequence hybridizable with the tagging portion of the PO.

According to a preferred embodiment, the PO is a 3'-tagged PO further comprising in its 3'-portion a tagging portion having a nucleotide sequence non-complementary to the target nucleic acid sequence or a 5'-tagged PO further comprising in its 5'-portion a tagging portion having a nucleotide sequence non-complementary to the target nucleic acid sequence, and the nucleotide sequence hybridizable with the PO in the CO comprises a nucleotide sequence hybridizable with a part of the tagging portion and a part of the targeting portion of the PO.

According to a preferred embodiment, the PO is a 3'-tagged PO further comprising in its 3'-portion a tagging portion having a nucleotide sequence non-complementary to the target nucleic acid sequence and the CO is immobilized onto the substrate through its 5'-end.

According to a preferred embodiment, the PO is a 5'-tagged PO further comprising in its 5'-portion a tagging portion having a nucleotide sequence non-complementary to the target nucleic acid sequence and the CO is immobilized onto the substrate through its 3'-end.

According to a preferred embodiment, the upstream oligonucleotide is an upstream primer or an upstream probe.

According to a preferred embodiment, the kit further comprises an enzyme having a 5' nuclease activity, more preferably a thermostable DNA polymerase having a 5' nuclease activity or FEN nuclease.

According to a preferred embodiment, the upstream oligonucleotide is located adjacently to the PO to the extent that the upstream oligonucleotide induces cleavage of the PO by an enzyme having a 5' nuclease activity.

According to a preferred embodiment, the upstream oligonucleotide has a partial-overlapped sequence with the targeting portion of the PO.

According to a preferred embodiment, the upstream primer induces through its extended strand the cleavage of the PO by the enzyme having the 5' nuclease activity.

According to a preferred embodiment, the upstream oligonucleotide is a upstream primer and the enzyme having the 5' nuclease activity is a template-dependent nucleic acid polymerase having a 5' nuclease activity.

According to a preferred embodiment, the kit further comprises an intercalating agent.

According to a preferred embodiment, the kit is used for detection of at least two types of target nucleic acid sequences. The upstream oligonucleotide comprises at least two types of upstream oligonucleotides, the PO comprises at least two types of POs and the CO comprises at least two types of CO.

According to a preferred embodiment, the kit further comprises a downstream primer.

In still further aspect of this invention, there is provided a kit for detecting a target nucleic acid sequence from a DNA or a mixture of nucleic acids by a POCH (PO Cleavage and Hybridization) assay on a solid substrate, comprising:

(a) a probing oligonucleotide (PO) comprising a targeting portion comprising a hybridizing nucleotide sequence complementary to the target nucleic acid sequence; and (b) a capturing oligonucleotide (CO) immobilized onto the solid substrate; wherein the CO comprises a nucleotide sequence hybridizable with the PO, whereby an PO uncleaved by an enzyme having a 5' nuclease activity is hybridized with the CO to form an uncleaved PO/CO duplex.

The features and advantages of this invention will be summarized as follows:

(a) The present invention detects a target nucleic acid sequence by use of in which the PO (Probing Oligonucleotide) hybridized with the target nucleic acid sequence is cleaved and the cleavage of the PO is detected by hybridization with the CO (Capturing Oligonucleotide). In the present invention, an uncleaved probe is hybridized with an oligonucleotide immobilized onto a solid substrate.

According to conventional technologies employing target probe and capturing probe immobilized, it is required to prevent uncleaved target probes from hybridizing with immobilized oligonucleotides by (i) designing the target probe to have a hairpin structure and controlling both conditions for hybridization with target sequences and conditions for hybridization with immobilized oligonucleotides; or (ii) designing immobilized oligonucleotides in considering immobilization orientation of immobilized oligonucleotides and their distance from the surface of a solid substrate. Therefore, the conventional methods are very inconvenient in terms of design of target probes and immobilized oligonucleotides and establishment of reaction conditions.

In contrast, the present invention is free from such inconveniences and limitations. The design of the PO and the CO is convenient and the optimization of reaction conditions is routinely easy in the present invention.

(b) Where the detection of signal on the solid substrate is continuously performed along with repetition of cleavage of the POs in the present invention, the number of the POs cleaved is increased upon the repetition number of the cleavage reaction and the signal is changed in parallel with the number of the POs cleaved. Then, the target nucleic acid sequence can be detected in a real-time manner.

(c) The present invention can detect simultaneously a plurality of target nucleic acid sequences even using solely one type of label. Since the cleavage of the PO is detected by hybridization with the CO immobilized onto the solid substrate, the PO for each target nucleic acid is not required to have different labels for detection of a plurality of target nucleic acid sequences.

(d) Generally, it would be understood by one of skill in the art that target detection methods using direct hybridization between target nucleic acid sequences and probes immobilized onto solid substrates may not obtain effective and accurate hybridization results because of restricted reaction environments that are inherent to a solid phase reaction. Unlikely, the present invention employs hybridization between the PO and the CO with no involving target nucleic acid sequences on a solid phase, providing more effective and accurate results in typical solid phase reaction environments and conditions.

(e) Where the present invention uses the tagged PO and the CO having a nucleotide sequence hybridizable with the tagging portion of the PO, the sequence of the tagging portion of the PO and the sequence of the CO can be selected in no consideration of a target nucleic acid sequence. This makes it possible to pre-design a pool of sequences useful in the present invention. In particular, the CO can be prepared in a ready-made fashion with no consideration or knowledge of target nucleic acid sequences. Such features provide prominent advantages on a microarray assay using COs immobilized onto a solid substrate.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of Probing Oligonucleotide Cleavage and Hybridization (POCH) Assay Using a Single-Labeled Non-Tagged Probing Oligonucleotide (PO)

A New assay, Probing Oligonucleotide Cleavage & Hybridization (POCH) assay, was evaluated for the detection of a target nucleic acid sequence using a single-labeled non-tagged PO (see FIG. 2). Cleavage of PO was conducted in a tube and an aliquot of the resultant was taken into a microarray where Capturing Oligonucleotide (CO) was immobilized.

Taq DNA polymerase having 5' nuclease activity was used for the extension of upstream primer and the cleavage of PO. The non-tagged PO comprises a targeting portion complement to the target nucleic acid sequence and has Quasar570 as a fluorescent reporter molecule at its 5'-end. The CO comprises a nucleotide sequence hybridizable with the targeting portion of the PO. The PO and CO are blocked with a carbon spacer at their 3'-ends. The CO has poly(T)$_{10}$ as a linker arm and was immobilized on the surface of a glass slide by using an amino group (AminnoC6) at its 5'-end. A marker probe having a fluorescent reporter molecule (Quasar570) at its 5'-end was immobilized on the surface of the glass slide by using an amino group at its 3'-end. Synthetic oligonucleotide for *Neisseria gonorrhoeae* (NG) was used as a template.

The sequences of synthetic template, upstream primer, PO, CO and marker used in this Example are:

```
NG-T
                                      (SEQ ID NO: 1)
5'-AAATATGCGAAACACGCCAATGAGGGGCATGATGCTTTCTTTTTGT

TCTTGCTCGGCAGAGCGAGTGATACCGATCCATTGAAAAA-3'

NG-R
                                      (SEQ ID NO: 2)
5'-CAATGGATCGGTATCACTCGC-3'

NG-PO-1
                                      (SEQ ID NO: 3)
5'-[Quasar570]TGCCCCTCATTGGCGTGTTTCG[C3 spacer]-3'

NG-CO-1
                                      (SEQ ID NO: 4)
5'-[AminoC6]TTTTTTTTTTCGAAACACGCCAATGAGGGGCA

[C3 spacer]-3'

Marker
                                      (SEQ ID NO: 5)
5'-[Quasar570]ATATATATAT[AminoC7]-3'
```

NSB9 NHS slides (NSBPOSTECH, Korea) were used for fabrication of the CO and marker (SEQ ID NOs: 4 and 5). The CO and marker dissolved in NSB spotting buffer at the final concentration of 50 µM were printed on the NSB9 NHS slides with PersonalArrayer™ 16 Microarray Spotter (CapitalBio, China). The CO and marker were spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound CO and marker, and rinsed with distilled water. Then, the DNA-functionalized slides were dried using a slide centrifuge and stored in dark at 4° C. until use.

The cleavage reaction was conducted in the final volume of 50 µl containing 2 pmole of synthetic template (SEQ ID NO: 1) for NG gene, 10 pmole of upstream primer (SEQ ID NO: 2), 1 pmole of PO (SEQ ID NO: 3), and 25 µl of 2× Master Mix containing 2.5 mM MgCl$_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C. and 60 sec at 60° C.

The 30 µl of the resulting mixture was applied to a chamber assembled on the surface of NSB glass slide on which the CO (SEQ ID NO: 4) was cross-linked. The slide was placed on in situ block in a thermocycler (GenePro B4I, China). The hybridization reaction was allowed for 30 min at 55° C. The image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 14, a decreased fluorescent signal (RFU: 9,006±20.5) was detected in the presence of the target nucleic acid sequence in comparison with the fluorescent signal (RFU: 65,484±0.7) in the absence of the target nucleic acid sequence.

These results indicate that POCH assay is applicable for the detection of a target nucleic acid sequence.

Example 2: Evaluation of POCH Assay Using a Single-Labeled 3'-Tagged PO

We further evaluated POCH assay for the detection of a target nucleic acid sequence using a single-labeled 3'-tagged PO (see FIG. 4). Cleavage of PO was conducted in a tube and an aliquot of the resultant was taken into a microarray where CO was immobilized.

Taq DNA polymerase having 5' nuclease activity was used for the extension of upstream primer and the cleavage of PO. The 3'-tagged PO comprises a targeting portion complement to the target nucleic acid sequence and a 3'-tagging portion not complement to the target nucleic acid sequence. The 3'-tagged PO has Quasar570 as a fluorescent reporter molecule at its 5'-end. The CO comprises a nucleotide sequence hybridizable with the 3'-tagging portion of the PO. The 3'-tagged PO and CO are blocked with a carbon spacer at their 3'-ends. The CO has poly(T)$_5$ as a linker arm and was immobilized on the surface of a glass slide by using an amino group (AminnoC6) at its 5'-end. A marker probe having a fluorescent reporter molecule (Quasar570) at its 5'-end was immobilized on the surface of the glass slide by using an amino group at its 3'-end. Synthetic oligonucleotide for *Neisseria gonorrhoeae* (NG) was used as a template.

The sequences of synthetic template, upstream primer, 3'-tagged PO, CO and marker used in this Example are:

NGT
(SEQ ID NO: 1)
5'-AAATATGCGAAACACGCCAATGAGGGGCATGATGCTTTCTTTTGT

TCTTGCTCGGCAGAGCGAGTGATACCGATCCATTGAAAAA-3'

NG-R
(SEQ ID NO: 2)
5'-CAATGGATCGGTATCACTCGC-3'

NG-PO-2
(SEQ ID NO: 6)
5'-[Quasar570]TGCCCCTCATTGGCGTGTTTCG<u>GACGACGGCTTGGC</u>

<u>TTTACGA</u>[C3 spacer]-3'

NG-CO-2
(SEQ ID NO: 7)
5'-[AminoC6]TTTTTTCGTAAAGCCAAGCCGTCGTC[C3 spacer]-3'

Marker
(SEQ ID NO: 5)
5'[Quasar570]ATATATATAT[AminoC7]-3'
(Underlined letters indicate the 3'-tagging portion of PO)

Slide preparation was conducted as the same protocol used in Example 1 except that CO of SEQ ID NO: 7 is used instead of that of SEQ ID NO: 4.

The cleavage reaction was conducted in the final volume of 50 µl containing 2 pmole of synthetic template (SEQ ID NO: 1) for NG gene, 10 pmole of upstream primer (SEQ ID NO: 2), 1 pmole of PO (SEQ ID NO: 6), and 25 µl of 2× Master Mix containing 2.5 mM $MgCl_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C. and 60 sec at 60° C.

The 30 µl of the resulting mixture was applied to a chamber assembled on the surface of NSB glass slide on which the CO (SEQ ID NO: 7) was cross-linked. The slide was placed on in situ block in a thermocycler (GenePro B4I, China). The hybridization reaction was allowed for 30 min at 55° C. The image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 15, a decreased fluorescent signal (RFU: 10,217±73.5) was detected in the presence of the target nucleic acid sequence in comparison with the fluorescent signal (RFU: 65,464±6.4) in the absence of the target nucleic acid sequence.

These results indicate that POCH assay using a single-labeled 3'-tagged PO is applicable for the detection of a target nucleic acid sequence.

Example 3: Evaluation of POCH Assay Using a Single-Labeled 5'-Tagged PO

We further evaluated POCH assay using a single-labeled 5'-tagged PO (see FIG. 5). Cleavage of PO was conducted in a tube and an aliquot of the resultant was taken into a microarray where CO was immobilized.

Taq DNA polymerase having 5' nuclease activity was used for the extension of upstream primer and the cleavage of PO. The 5'-tagged PO comprises a targeting portion complement to the target nucleic acid sequence and a 5'-tagging portion not complement to the target nucleic acid sequence. The 5'-tagged PO has a Quasar570 as a fluorescent reporter molecule at its 3'-end. CO comprises a nucleotide sequence hybridizable with the 5'-tagging portion of the PO. The CO has poly$(T)_{10}$ as a linker arm and was immobilized on the surface of a glass slide by using an amino group (AminnoC7) at its 3'-end. A marker probe having a fluorescent reporter molecule (Quasar570) at its 5'-end was immobilized on the surface of the glass slide by using an amino group at its 3'-end. Synthetic oligonucleotide for *Neisseria gonorrhoeae* (NG) was used as a template.

The sequences of synthetic template, upstream primer, 5'-tagged PO, CO and marker used in this Example are:

NGT
(SEQ ID NO: 1)
5'-AAATATGCGAAACACGCCAATGAGGGGCATGATGCTTTCTTTTGT

TCTTGCTCGGCAGAGCGAGTGATACCGATCCATTGAAAAA-3'

NG-R
(SEQ ID NO: 2)
5'-CAATGGATCGGTATCACTCGC-3'

NG-PO-3
(SEQ ID NO: 8)
5'-<u>ACGACGGCTTGGC</u>TGCCCCTCATTGGCGTGTTTCG

[Quasar570]-3'

NG-CO-3
(SEQ ID NO: 9)
5'-GCCAAGCCGTCGTTTTTTTTTTT[AminoC7]-3'

Marker
(SEQ ID NO: 5)
5'[Quasar570]ATATATATAT[AminoC7]-3'
(Underlined letters indicate the 5'-tagging portion of PO)

Slide preparation was conducted as the same protocol used in Example 1, except that CO of SEQ ID NO: 9 is used instead of that of SEQ ID NO: 4.

The cleavage reaction was conducted in the final volume of 50 µl containing 2 pmole of synthetic template (SEQ ID NO: 1) for NG gene, 10 pmole of upstream primer (SEQ ID NO: 2), 1 pmole of PO (SEQ ID NO: 8), and 25 µl of 2× Master Mix containing 2.5 mM $MgCl_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C. and 60 sec at 60° C.

The 30 µl of the resulting mixture was applied to a chamber assembled on the surface of NSB glass slide on which the CO (SEQ ID NO: 9) was cross-linked. The slide was placed on in situ block in a thermocycler (GenePro B4I, China). The hybridization reaction was allowed for 30 min at 55° C. The image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 16, a decreased fluorescent signal (RFU: 17,586±152.0) was detected in the presence of the target nucleic acid sequence in comparison with the fluorescent signal (RFU: 65,455±0.7) in the absence of the target nucleic acid sequence.

These results indicate that POCH assay using a single-labeled 5'-tagged PO is applicable for the detection of a target nucleic acid sequence.

Example 4: Evaluation of POCH Assay Using a Dual-Labeled 3'-Tagged PO

We further evaluated POCH assay for the detection of a target nucleic acid sequence using a dual-labeled 3'-tagged PO (see FIG. 11). Cleavage of PO was conducted in a tube and an aliquot of the resultant was taken into a microarray where CO was immobilized.

Taq DNA polymerase having 5' nuclease activity was used for the extension of upstream primer and the cleavage of PO. The 3'-tagged PO comprises a targeting portion complement to the target nucleic acid sequence and a 3'-tagging portion not complement to the target nucleic acid sequence. The 3'-tagged PO has a BHQ-2 as an acceptor molecule at it 5'-end and a Quasar570 as a donor molecule at its 3'-end of the targeting portion. CO comprises a nucleotide sequence hybridizable with the 3'-tagging portion of the PO. A signal from the donor molecule was measured for the detection of the target nucleic acid sequence. The 3'-tagged PO and CO are blocked with a carbon spacer at their 3'-ends. The CO has poly(T)$_5$ as a linker arm and was immobilized on the surface of a glass slide by using an amino group (AminnoC6) at its 5'-end. A marker probe having a fluorescent reporter molecule (Quasar570) at its 5'-end was immobilized on the surface of the glass slide by using an amino group at its 3'-end. Synthetic oligonucleotide for *Neisseria gonorrhoeae* (NG) was used as a template.

The sequences of synthetic template, upstream primer, 3'-tagged PO, CO and marker used in this Example are:

```
NG-T
                                        (SEQ ID NO: 1)
5'-AAATATGCGAAACACGCCAATGAGGGGCATGATGCTTTCTTTTTGT

TCTTGCTCGGCAGAGCGAGTGATACCGATCCATTGAAAAA-3'

NG-R
                                        (SEQ ID NO: 2)
5'-CAATGGATCGGTATCACTCGC-3'

NG-PO-4
                                       (SEQ ID NO: 10)
5'-[BHQ-2]TGCCCCTCATTGGCGTGTTTCG[T(Quasar570)]GAC GACGGCTTGGCTTTACGA[C3 spacer]-3'

NG-CO-2
                                        (SEQ ID NO: 7)
5'-[AminoC6]TTTTTTCGTAAAGCCAAGCCGTCGTC[C3 spacer]-

3'

Marker
                                        (SEQ ID NO: 5)
5'-[Quasar570]ATATATATAT[AminoC7]-3'
(Underlined letters indicate the 3'-tagging
portion of PO)
```

Slide preparation was conducted as the same protocol used in Example 1, except that CO of SEQ ID NO: 7 is used instead of that of SEQ ID NO: 4.

The cleavage reaction was conducted in the final volume of 50 µl containing 2 pmole of synthetic template (SEQ ID NO: 1) for NG gene, 10 pmole of upstream primer (SEQ ID NO: 2), 1 pmole of PO (SEQ ID NO: 10), and 25 µl of 2× Master Mix containing 2.5 mM MgCl$_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C. and 60 sec at 60° C.

The 30 µl of the resulting mixture was applied to a chamber assembled on the surface of NSB glass slide on which the CO (SEQ ID NO: 7) was cross-linked. The slide was placed on in situ block in a thermocycler (GenePro B4I, China). The hybridization reaction was allowed for 30 min at 55° C. The image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

Since the acceptor quenches the fluorescent signal from the donor, there is no signal from the donor in the uncleaved 3'-tagged PO/CO duplex. Whereas the donor-containing fragment of cleaved 3'-tagged PO hybridized with the CO is able to provide a fluorescent signal.

As shown in FIG. 17, an increased fluorescent signal (RFU: 65,469±0.7) was observed in the presence of the target nucleic acid sequence in comparison with the fluorescent signal (RFU: 13,349±441.2) in the absence of the target nucleic acid sequence.

These results indicate that POCH assay using a dual-labeled 3'-tagged PO is applicable for the detection of a target nucleic acid sequence.

Example 5: Detection of a Target Nucleic Acid Sequence by POCH Assay

We applied POCH assay to detect a target nucleic acid sequence accompanied with the target sequence amplification. A single-labeled non-tagged PO and a single-labeled 3'-tagged PO were used respectively to examine this application. Cleavage of PO during the target amplification by PCR process was conducted in a tube and an aliquot of the resultant was taken into a microarray where CO was immobilized.

Upstream primer is involved in the PO cleavage by an enzyme having a 5' nuclease activity and also involved in amplification of the target acid sequence with downstream primer by PCR process. Taq DNA polymerase having a 5' nuclease activity was used for the extension of upstream primer and downstream primer, and the cleavage of PO.

The non-tagged PO comprises a targeting portion complement to the target nucleic acid sequence. The CO for the non-tagged PO comprises a nucleotide sequence hybridizable with the targeting portion of the PO. The 3'-tagged PO comprises a targeting portion complement to the target nucleic acid sequence and a 3'-tagging portion not complement to the target nucleic acid sequence. The CO for the 3'-tagged PO comprises a nucleotide sequence hybridizable with the 3'-tagging portion of the PO.

The non-tagged PO and 3'-tagged PO have Quasar570 as a fluorescent reporter molecule at their 5'-ends. The POs and COs are blocked with a carbon spacer at their 3'-ends. The CO for the non-tagged PO has poly(T)$_{10}$ as a linker arm and was immobilized on the surface of a glass slide by using an amino group (AminnoC6) at its 5'-end. The CO for the 3'-tagged PO has poly(T)$_5$ as a linker arm and was immobilized on the surface of a glass slide by using an amino group (AminnoC6) at its 5'-end. A marker probe having a fluorescent reporter molecule (Quasar570) at its 5'-end was immobilized on the surface of the glass slide by using an amino group at its 3'-end. Genomic DNA of *Neisseria gonorrhoeae* (NG) was used as a target template.

5-1. POCH Assay Using Single-Labeled Non-Tagged PO

The sequences of upstream primer, downstream primer, PO, CO and marker used in this Example are:

```
NG-F
                                        (SEQ ID NO: 11)
5'-TACGCCTGCTACTTTCACGCT-3'

NG-R
                                        (SEQ ID NO: 2)
5'-CAATGGATCGGTATCACTCGC-3'

NG-PO-1
                                        (SEQ ID NO: 3)
5'-[Quasar570]TGCCCCTCATTGGCGTGTTTCG[C3 spacer]-3'

NG-CO-1
                                        (SEQ ID NO: 4)
5'-[AminoC6]TTTTTTTTTTCGAAACACGCCAATGAGGGGCA

[C3 spacer]-3'

Marker
                                        (SEQ ID NO: 5)
5'-[Quasar570]ATATATATAT[AminoC7]-3'
```

Slide preparation was conducted as the same protocol used in Example 1.

The cleavage reaction was conducted in the final volume of 50 μl containing each 100 pg genomic DNA of NG, 10 pmole of downstream primer (SEQ ID NO: 11), 10 pmole of upstream primer (SEQ ID NO: 2), 1 pmole of PO (SEQ ID NO: 3), and 25 μl of 2× Master Mix containing 2.5 mM MgCl$_2$, 200 μM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C. and 60 sec at 60° C. The 30 μl of the resulting mixture was applied to a chamber assembled on the surface of NSB glass slide on which the CO (SEQ ID NO: 4) were crosslinked. The slide was placed on in situ block in a thermocycler (GenePro B4I, China). The hybridization reaction was allowed for 30 min at 55° C. The image acquisition was carried out after each washing by the use of Confocal Laser Scanner, Axon GenePix4300A (Molecular Device, US) with scanning at 5 μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 18, a decreased fluorescent signal (RFU: 1,650±97.6) was observed in the presence of the target nucleic acid sequence in comparison with the fluorescent signal (RFU: 64,474±0.0) in the absence of the target nucleic acid sequence.

5-2. POCH Assay Using Single-Labeled 3'-Tagged PO

The sequences of upstream primer, downstream primer, 3'-tagged PO, CO and marker used in this Example are:

```
NG-F
                                        (SEQ ID NO: 11)
5'-TACGCCTGCTACTTTCACGCT-3'

NG-R
                                        (SEQ ID NO: 2)
5'-CAATGGATCGGTATCACTCGC-3'

NG-PO-2
                                        (SEQ ID NO: 6)
5'[Quasar570]TGCCCCTCATTGGCGTGTTTCGGACGACGGCTTGGC TTTACGA[C3 spacer]-3'

NG-CO-2
                                        (SEQ ID NO: 7)
5'-[AminoC6]TTTTTTCGTAAAGCCAAGCCGTCGTC[C3 spacer]-

3'

Marker
                                        (SEQ ID NO: 5)
5'-[Quasar570]ATATATATAT[AminoC7]-3'
(Underlined letters indicate the 3'-tagging
portion of PO)
```

Slide preparation was conducted as the same protocol used in Example 2.

The cleavage reaction was conducted in the final volume of 50 μl containing each 100 pg genomic DNA of NG, 10 pmole of downstream primer (SEQ ID NO: 11), 10 pmole of upstream primer (SEQ ID NO: 2), 1 pmole of PO (SEQ ID NO: 6), and 25 μl of 2× Master Mix containing 2.5 mM MgCl$_2$, 200 μM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 60 cycles of 30 sec at 95° C. and 60 sec at 60° C. The 30 μl of the resulting mixture was applied to a chamber assembled on the surface of NSB glass slide on which the CO (SEQ ID NO: 7) were crosslinked. The slide was placed on in situ block in a thermocycler (GenePro B4I, China). The hybridization reaction was allowed for 30 min at 55° C. The image acquisition was carried out after each washing by the use of Confocal Laser Scanner, Axon GenePix4300A (Molecular Device, US) with scanning at 5 μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 19, a decreased fluorescent signal (RFU: 9,969±217.1) was observed in the presence of the target nucleic acid sequence in comparison with the fluorescent signal (RFU: 65,470±1.4) in the absence of the target nucleic acid sequence.

These results indicate that a target nucleic acid sequence can be detected by POCH assay accompanied with target amplification by PCR process.

Example 6: Real-Time Detection of a Target Nucleic Acid Sequence by POCK Assay We applied POCH assay for real-time detection of a target nucleic acid sequence. A 3'-tagged PO was used to examine this application. Cleavage of PO and hybridization of PO with CO were conducted with target amplification by PCR process on a microarray where CO was immobilized. The change of a fluorescent signal depending on cycle numbers was measured. Genomic DNA of *Neisseria gonorrhoeae* (NG) was used as a target template.

The same oligonucleotides (upstream primer, downstream primer, 3'-tagged PO, CO and marker) used in Example 5-2 were used in this Example. Slide preparation was conducted as the same protocol used in Example 2.

A mixture for the POCH assay was prepared in the final volume of 30 µl containing 100 pg genomic DNA of NG, 10 pmole of downstream primer (SEQ ID NO: 11), 10 pmole of upstream primer (SEQ ID NO: 2), 1 pmole of PO (SEQ ID NO: 6), and 25 µl of 2× Master Mix containing 2.5 mM $MgCl_2$, 200 µM of dNTPs, and 4 units of H-Taq DNA polymerase (Solgent, Korea); the whole mixture was applied to a chamber assembled on the surface of NSB glass slide on which the CO was cross-linked (SEQ ID NO: 7). The slide was placed on in situ block in a thermocycler (GenePro B4I, China). Five same slides were prepared for cycling analysis. The POCH reaction was carried out as follows: 15 min denaturation at 95° C. and 0, 20, 30, 40 or 60 cycles of 30 sec at 95° C., 60 sec at 60° C. and 30 min at 55° C. After the corresponding cycle number, the image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

Figure 20B:
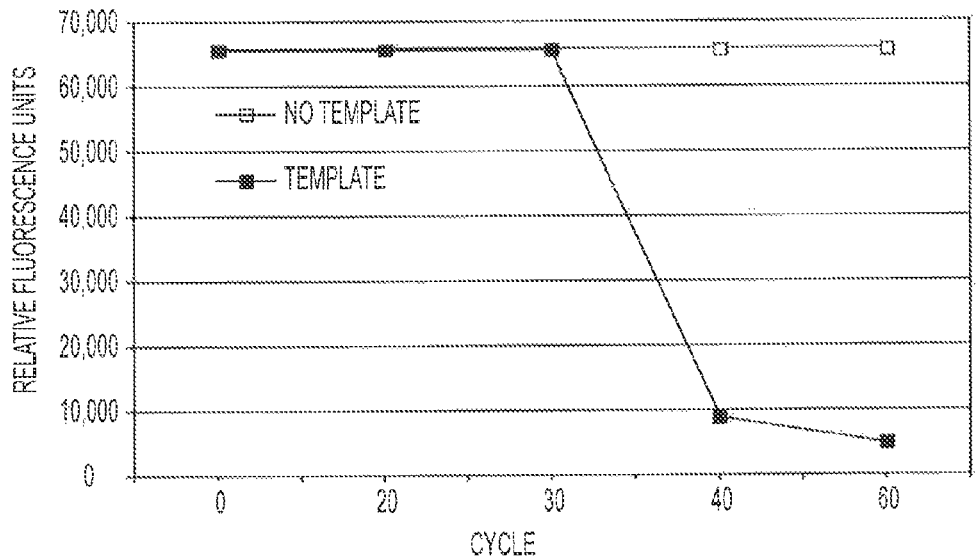

As shown in FIGS. 20A and 20B, the fluorescent signal was decreased after 30 cycles (0 cycle_RFU: 65,438±0.0; 20 cycles_RFU: 65,445±2.1; 30 cycles_RFU: 65,480±0.0; 40 cycles_RFU: 8,844±1,485.6; and 60 cycles_RFU: 4,878±169.7) in the presence of the template. There was no change of the fluorescent signal depending on cycle numbers in the absence of the template.

These results indicate that a target nucleic acid sequence can be detected in a real-time manner by POCH assay.

Example 7: Evaluation of POCH Assay Using Upstream Oligonucleotide-Independent Cleavage of PO We further evaluated POCH assay for the detection of a target nucleic acid sequence without upstream oligonucleotide. Upstream oligonucleotide-independent cleavage of PO was conducted without an upstream oligonucleotide in a tube and an aliquot of the resultant was taken into a microarray where CO was immobilized.

Taq DNA polymerase having 5' nuclease activity was used for the upstream oligonucleotide-independent cleavage of PO. The non-tagged PO comprises a targeting portion complement to the target nucleic acid sequence and has FAM as a fluorescent reporter molecule at its 5'-end. The CO comprises a nucleotide sequence hybridizable with the targeting portion of the PO. The PO and CO are blocked with a carbon spacer at their 3'-ends. The CO has poly(T)$_{10}$ as a linker arm and was immobilized on the surface of a glass slide by using an amino group (Amino C6) at its 5'-end. A marker probe having a fluorescent reporter molecule (Quasar570) at its 5'-end was immobilized on the surface of the glass slide by using an amino group at its 3'-end. Synthetic oligonucleotide for *Neisseria gonorrhoeae* (NG) was used as a template.

The sequences of synthetic template, PO, CO and marker used in this Example are:

```
NGT
                                    (SEQ ID NO: 1)
5'-AAATATGCGAAACACGCCAATGAGGGGCATGATGCTTTCTTTTGTT

CTTGCTCGGCAGAGCGAGTGATACCGATCCATTGAAAAA-3'

NG-PO-5
                                    (SEQ ID NO: 12)
5'-[FAM]TGCCCCTCATTGGCGTGTTTCG[C3 spacer]-3'

NG-CO-1
                                    (SEQ ID NO: 4)
5'-[AminoC6]TTTTTTTTTTCGAAACACGCCAATGAGGGGCA

[C3 spacer]-3'

Marker
                                    (SEQ ID NO: 5)
5'-[Quasar570]ATATATATAT[AminoC7]-3'
```

NSB9 NHS slides (NSBPOSTECH, Korea) were used for fabrication of the CO and marker (SEQ ID NOs: 4 and 5). The CO and marker dissolved in NSB spotting buffer at the final concentration of 50 µM were printed on the NSB9 NHS slides with PersonalArrayer™ 16 Microarray Spotter (CapitalBio, China). The CO and marker were spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound CO and marker, and rinsed with distilled water. Then, the DNA-functionalized slides were dried using a slide centrifuge and stored in dark at 4° C. until use.

The cleavage reaction was conducted in the final volume of 50 µl containing 2 pmole of synthetic template (SEQ ID NO: 1) for NG gene, 1 pmole of PO (SEQ ID NO: 12), and 25 µl of 2× Master Mix containing 2.5 mM $MgCl_2$, 200 µM of dNTPs, and 4 units of H-Taq DNA polymerase (Solgent, Korea); the tube containing the reaction mixture was placed in the real-time thermocycler (CFX96, Bio-Rad); the reaction mixture was denatured for 15 min at 95° C. and subjected to 30 cycles of 30 sec at 95° C. and 60 sec at 60° C.

The 30 µl of the resulting mixture was applied to a chamber assembled on the surface of NSB glass slide on which the CO (SEQ ID NO: 4) was cross-linked. The slide was placed on in situ block in a thermocycler (GenePro B4I, China). The hybridization reaction was allowed for 30 min at 55° C. The image acquisition was carried out by the use of Confocal Laser Scanner, Axon GenePix4300A (Molecular Device, US) with scanning at 5 µm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was duplicated for the test of reproducibility. The fluorescence intensity indicates the average value of the duplicated spots.

A decreased fluorescent signal was detected in the presence of the target, nucleic acid sequence in comparison with the fluorescent signal in the absence of the target nucleic acid sequence.

These results indicate that POCH assay using upstream oligonucleotide-independent cleavage of PO is applicable for the detection of a target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting at least one target nucleic acid molecule having sequence information from a DNA or a mixture of nucleic acids in a sample by a POCH (PO Cleavage and Hybridization) assay on a solid substrate, comprising:
   (a) hybridizing the sequence of said target nucleic acid molecule with an upstream oligonucleotide and a probing oligonucleotide (PO); wherein the upstream oligonucleotide comprises a hybridizing nucleotide sequence complementary to the sequence of said target nucleic acid molecule; the PO comprises a targeting portion comprising a hybridizing nucleotide sequence complementary to the sequence of said target nucleic acid molecule; the PO has a single label; the upstream oligonucleotide is located upstream of the PO; the upstream oligonucleotide or its extended strand induces cleavage of the PO by an enzyme having a 5' nuclease activity;
   (b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to produce a single label-containing fragment;
   (c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex; and
   (d) detecting a signal from the single label on the solid substrate; wherein (i) when a signal difference is observed by comparing the signal from the single label on the solid substrate to a signal from a control that does not contain the target nucleic acid sequence, the signal difference indicates the presence of the target nucleic acid sequence, or (ii) when a signal change is observed at cycles with predetermined interval by detecting the signal from the single label on the solid substrate along with repetition of the steps (a)-(b), (a)-(c) or (a)-(d), the signal change indicates the presence of the target nucleic acid sequence.

2. The method according to claim 1, wherein the nucleotide sequence hybridizable with the PO in the CO comprises a nucleotide sequence hybridizable with the targeting portion of the PO.

3. The method according to claim 1, wherein the PO is a 3'-tagged PO further comprising in its 3'-portion a tagging portion having a nucleotide sequence non-complementary to the sequence of said target nucleic acid molecule or a 5'-tagged PO further comprising in its 5'-portion a tagging portion having a nucleotide sequence non-complementary to the sequence of said target nucleic acid molecule, and the nucleotide sequence hybridizable with the PO in the CO comprises a nucleotide sequence hybridizable with the tagging portion of the PO.

4. The method according to claim 3, wherein the single label is positioned such that the single label is not remained on a tagging portion-containing fragment released by cleavage of the PO.

5. The method according to claim 1, wherein the PO is a 3'-tagged PO further comprising in its 3'-portion a tagging portion having a nucleotide sequence non-complementary to the sequence of said target nucleic acid molecule or a 5'-tagged PO further comprising in its 5'-portion a tagging portion having a nucleotide sequence non-complementary to the sequence of said target nucleic acid molecule, and the nucleotide sequence hybridizable with the PO in the CO comprises a nucleotide sequence hybridizable with a part of the tagging portion and a part of the targeting portion of the PO.

6. The method according to claim 1, wherein the PO and/or CO is blocked at its 3'-end to prohibit its extension.

7. The method according to claim 1, wherein the upstream oligonucleotide is an upstream primer or an upstream probe.

8. The method according to claim 1, wherein the upstream oligonucleotide has a partial-overlapped sequence with the targeting portion of the PO.

9. The method according to claim 1, wherein the enzyme having the 5' nuclease activity is a thermostable DNA polymerase having a 5' nuclease activity or FEN nuclease.

10. The method according to claim 1, wherein the upstream oligonucleotide is a upstream primer and the enzyme having the 5' nuclease activity is a template-dependent nucleic acid polymerase having a 5' nuclease activity.

11. The method according to claim 1, wherein the method further comprises repeating the steps (a)-(b), (a)-(c) or (a)-(d) with denaturation between repeating cycles.

12. The method according to claim 1, wherein the steps (a)-(d) are performed in a reaction vessel or in separate reaction vessels.

13. The method according to claim 1, wherein the sequence of said target nucleic acid molecule comprises at least two types of target nucleic acid molecule.

14. The method according to claim 1, wherein the sequence of said target nucleic acid molecule comprises a nucleotide variation.

15. The method according to claim 1, wherein the method is performed in the presence of a downstream primer.

16. A method for detecting at least one target nucleic acid molecule having sequence information from a DNA or a mixture of nucleic acids in a sample by a POCH (PO Cleavage and Hybridization) assay on a solid substrate, comprising:
   (a) hybridizing the sequence of said target nucleic acid molecule with an upstream oligonucleotide and a probing oligonucleotide (PO); wherein the upstream oligonucleotide comprises a hybridizing nucleotide sequence complementary to the sequence of said target nucleic acid molecule; the PO comprises a targeting portion comprising a hybridizing nucleotide sequence complementary to the sequence of said target nucleic acid molecule; the PO has an interactive dual label comprising a donor molecule and an acceptor molecule; the upstream oligonucleotide is located upstream of the PO; the upstream oligonucleotide or its extended strand induces cleavage of the PO by an enzyme having a 5' nuclease activity;

(b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to separate the interactive dual label, whereby a donor-containing fragment and an acceptor-containing fragment are produced;

(c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that at least one of the donor-containing fragment and the acceptor-containing fragment is not hybridized with the CO and an uncleaved PO is hybridized with the CO to form an uncleaved PO/CO duplex; wherein a signal from the uncleaved PO/CO duplex is differentiated from a signal provided at the time that at least one of the donor-containing fragment and the acceptor-containing fragment is not hybridized with the CO; and (d) detecting a signal from the interactive dual label on the solid substrate; wherein (i) when a signal difference is observed by comparing the signal from the interactive dual label on the solid substrate to a signal from a control that does not contain the target nucleic acid sequence, the signal difference indicates the presence of the target nucleic acid sequence, or (ii) when a signal change is observed at cycles with predetermined interval by detecting the signal from the interactive dual label on the solid substrate along with repetition of the steps (a)-(b), (a)-(c) or (a)-(d), the signal change indicates the presence of the target nucleic acid sequence.

17. The method according to claim 16, wherein the nucleotide sequence hybridizable with the PO in the CO comprises a nucleotide sequence hybridizable with the targeting portion of the PO, and the interactive dual label is located to the extent that a signal from the donor molecule is quenched by the acceptor molecule when the uncleaved PO/CO duplex is formed, wherein the step (d) is performed by detecting a signal from the acceptor molecule.

18. The method according to claim 16, wherein the PO is a 3'-tagged PO further comprising in its 3'-portion a tagging portion having a nucleotide sequence non-complementary to the sequence of said target nucleic acid molecule or a 5'-tagged PO further comprising in its 5'-portion a tagging portion having a nucleotide sequence non-complementary to the sequence of said target nucleic acid molecule, and the nucleotide sequence hybridizable with the PO in the CO comprises a nucleotide sequence hybridizable with the tagging portion of the PO, and the interactive dual label is located to the extent that a signal from the donor molecule is quenched by the acceptor molecule when the uncleaved PO/CO duplex is formed, wherein the step (d) is performed by detecting a signal from the acceptor molecule.

19. The method according to claim 16, wherein the nucleotide sequence hybridizable with the PO in the CO comprises a nucleotide sequence hybridizable with the targeting portion of the PO, and the hybridization reaction in the step (c) is performed under conditions such that the donor-containing fragment is not hybridized with the CO; wherein the interactive dual label is located to the extent that a signal from the donor molecule is unquenched by the acceptor molecule when the uncleaved PO/CO duplex is formed and the step (d) is performed by detecting a signal from the donor molecule.

20. The method according to claim 16, wherein the PO is a 3'-tagged PO further comprising in its 3'-portion a tagging portion having a nucleotide sequence non-complementary to the sequence of said target nucleic acid molecule or a 5'-tagged PO further comprising in its 5'-portion a tagging portion having a nucleotide sequence non-complementary to the sequence of said target nucleic acid molecule; the nucleotide sequence hybridizable with the PO in the CO comprises a nucleotide sequence hybridizable with the tagging portion of the PO; the donor-containing fragment comprises the tagging portion hybridizable with the CO and in the hybridization reaction in the step (c), the donor-containing fragment is hybridized with the CO; wherein the interactive dual label is located to the extent that a signal from the donor molecule is quenched by the acceptor molecule when the uncleaved PO/CO duplex is formed and the step (d) is performed by detecting a signal from the donor molecule.

21. The method according to claim 16, wherein the PO is a 3'-tagged PO further comprising in its 3'-portion a tagging portion having a nucleotide sequence non-complementary to the sequence of said target nucleic acid molecule or a 5'-tagged PO further comprising in its 5'-portion a tagging portion having a nucleotide sequence non-complementary to the sequence of said target nucleic acid molecule, and the nucleotide sequence hybridizable with the PO in the CO comprises a nucleotide sequence hybridizable with a part of the tagging portion and a part of the targeting portion of the PO.

22. The method according to claim 16, wherein the upstream oligonucleotide is a upstream primer and the step (b) uses a template-dependent nucleic acid polymerase for the extension of the upstream primer.

23. The method according to claim 16, wherein the method further comprises repeating the steps (a)-(b), (a)-(c) or (a)-(d) with denaturation between repeating cycles.

24. The method according to claim 16, wherein the steps (a)-(d) are performed in a reaction vessel or in separate reaction vessels.

25. The method according to claim 16, wherein the method is performed in the presence of a downstream primer.

26. A method for detecting at least one target nucleic acid molecule having sequence information from a DNA or a mixture of nucleic acids in a sample by a POCH (PO Cleavage and Hybridization) assay on a solid substrate, comprising:

(a) hybridizing the sequence of said target nucleic acid molecule with an upstream oligonucleotide and a probing oligonucleotide (PO); wherein the upstream oligonucleotide comprises a hybridizing nucleotide sequence complementary to the sequence of said target nucleic acid molecule; the PO comprises a targeting portion comprising a hybridizing nucleotide sequence complementary to the sequence of said target nucleic acid molecule; the upstream oligonucleotide is located upstream of the PO; the upstream oligonucleotide or its extended strand induces cleavage of the PO by an enzyme having a 5' nuclease activity;

(b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to produce a cleaved fragment;

(c) performing a hybridization reaction in the presence of an intercalating agent by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the cleaved fragment is not hybridized with the CO and an uncleaved PO is hybridized with the CO to form an uncleaved PO/CO duplex; and (d) detecting a signal from the intercalating agent on the solid substrate; wherein (i) when a signal difference is observed by comparing the signal from the intercalating agent on the solid substrate to a signal from a control that does not contain the target nucleic acid sequence, the signal difference indicates the presence of the target nucleic acid sequence, or (ii) when a signal change is observed at cycles with predetermined interval by detecting the signal from the intercalating agent on the solid substrate along with repetition of the steps (a)-(b), (a)-(c) or (a)-(d), the signal change indicates the presence of the target nucleic acid sequence.

27. The method according to claim 26, wherein the nucleotide sequence hybridizable with the PO in the CO comprises a nucleotide sequence hybridizable with the targeting portion of the PO.

28. The method according to claim 26, wherein the upstream oligonucleotide is a upstream primer and the step (b) uses a template-dependent nucleic acid polymerase for the extension of the upstream primer.

29. The method according to claim 26, wherein the method further comprises repeating the steps (a)-(b), (a)-(c) or (a)-(d) with denaturation between repeating cycles.

30. The method according to claim 26, wherein the steps (a)-(d) are performed in a reaction vessel or in separate reaction vessels.

31. The method according to claim 26, wherein the method is performed in the presence of a downstream primer.

32. A method for detecting at least one target nucleic acid molecule having sequence information from a DNA or a mixture of nucleic acids in a sample by a POCH (PO Cleavage and Hybridization) assay on a solid substrate, comprising:

(a) hybridizing the sequence of said target nucleic acid molecule with a probing oligonucleotide (PO); wherein the the PO comprises a targeting portion comprising a hybridizing nucleotide sequence complementary to the sequence of said target nucleic acid molecule; the PO has a single label;

(b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to produce a single label-containing fragment (c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the single label-containing fragment is not hybridized with the CO and an uncleaved PO is hybridized with the CO to form an uncleaved PO/CO duplex; and (d) detecting a signal from the single label on the solid substrate; wherein (i) when a signal difference is observed by comparing the signal from the single label on the solid substrate to a signal from a control that does not contain the target nucleic acid sequence, the signal difference indicates the presence of the target nucleic acid sequence, or (ii) when a signal change is observed at cycles with predetermined interval by detecting the signal from the single label on the solid substrate along with repetition of the steps (a)-(b), (a)-(c) or (a)-(d), the signal change indicates the presence of the target nucleic acid sequence.

33. A method for detecting at least one target nucleic acid molecule having sequence information from a DNA or a mixture of nucleic acids in a sample by a POCH (PO Cleavage and Hybridization) assay on a solid substrate, comprising:

(a) hybridizing the sequence of said target nucleic acid molecule with a probing oligonucleotide (PO); wherein the PO comprises a targeting portion comprising a hybridizing nucleotide sequence complementary to the sequence of said target nucleic acid molecule; the PO has an interactive dual label comprising a donor molecule and an acceptor molecule;

(b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to separate the interactive dual label, whereby a donor-containing fragment and an acceptor-containing fragment are produced (c) performing a hybridization reaction by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that at least one of the donor-containing fragment and the acceptor-containing fragment is not hybridized with the CO and an uncleaved PO is hybridized with the CO to form an uncleaved PO/CO duplex; wherein a signal from the uncleaved PO/CO duplex is differentiated from a signal provided at the time that at least one of the donor-containing fragment and the acceptor-containing fragment is not hybridized with the CO; and (d) detecting a signal from the interactive dual label on the solid substrate; wherein (i) when a signal difference is observed by comparing the signal from the interactive dual label on the solid substrate to a signal from a control that does not contain the target nucleic acid sequence, the signal difference indicates the presence of the target nucleic acid sequence, or (ii) when a signal change is observed at cycles with predetermined interval by detecting the signal from the interactive dual label on the solid substrate along with repetition of the steps (a)-(b), (a)-(c) or (a)-(d), the signal change indicates the presence of the target nucleic acid sequence.

34. A method for detecting at least one target nucleic acid molecule having sequence information from a DNA or a mixture of nucleic acids in a sample by a POCH (PO Cleavage and Hybridization) assay on a solid substrate, comprising:
  (a) hybridizing the sequence of said target nucleic acid molecule with a probing oligonucleotide (PO); wherein the PO comprises a targeting portion comprising a hybridizing nucleotide sequence complementary to the sequence of said target nucleic acid molecule;
  (b) contacting the resultant of the step (a) to the enzyme having the 5' nuclease activity under conditions for cleavage of the PO; wherein when the PO is hybridized with the sequence of said target nucleic acid molecule, the PO is cleaved by the enzyme having the 5' nuclease activity to produce a cleaved fragment;
  (c) performing a hybridization reaction in the presence of an intercalating agent by contacting the resultant of the step (b) to a capturing oligonucleotide (CO) immobilized onto the solid substrate; wherein the CO comprises a nucleotide sequence hybridizable with the PO; wherein the hybridization reaction is performed under conditions such that the cleaved fragment is not hybridized with the CO and an uncleaved PO is hybridized with the CO to form an uncleaved PO/CO duplex; and
  (d) detecting a signal from the intercalating agent on the solid substrate; wherein (i) when a signal difference is observed by comparing the signal from the intercalating agent on the solid substrate to a signal from a control that does not contain the target nucleic acid sequence, the signal difference indicates the presence of the target nucleic acid sequence, or (ii) when a signal change is observed at cycles with predetermined interval by detecting the signal from the intercalating agent on the solid substrate along with repetition of the steps (a)-(b), (a)-(c) or (a)-(d), the signal change indicates the presence of the target nucleic acid sequence.

* * * * *

SEQUENCE LISTING

```
<160> NUMBER OF SEQ ID NOS: 12

<210> SEQ ID NO 1
<211> LENGTH: 86
<212> TYPE: DNA
<213> ORGANISM: Artificial Sequence
<220> FEATURE:
<223> OTHER INFORMATION: Neisseria gonorrhoeae synthetic template (NG-T)

<400> SEQUENCE: 1
aaatatgcga aacacgccaa tgaggggcat gatgctttct ttttgttctt gctcggcaga      60
gcgagtgata ccgatccatt gaaaaa                                           86

<210> SEQ ID NO 2
<211> LENGTH: 21
<212> TYPE: DNA
<213> ORGANISM: Artificial Sequence
<220> FEATURE:
<223> OTHER INFORMATION: Neisseria gonorrhoeae upstream primer (NG-R)

<400> SEQUENCE: 2
caatggatcg gtatcactcg c                                                21

<210> SEQ ID NO 3
<211> LENGTH: 22
<212> TYPE: DNA
<213> ORGANISM: Artificial Sequence
<220> FEATURE:
<223> OTHER INFORMATION: Neisseria gonorrhoeae Probing Oligonucleotide 1
      (NG-PO-1)

<400> SEQUENCE: 3
tgcccctcat tggcgtgttt cg                                               22

<210> SEQ ID NO 4
<211> LENGTH: 32
<212> TYPE: DNA
<213> ORGANISM: Artificial Sequence
<220> FEATURE:
<223> OTHER INFORMATION: Neisseria gonorrhoeae Capturing Oligonucleotide
      1 (NG-CO-1)

<400> SEQUENCE: 4 ttttttttt cgaaacacgc caatgagggg ca                                     32

<210> SEQ ID NO 5
<211> LENGTH: 10
<212> TYPE: DNA
<213> ORGANISM: Artificial Sequence
<220> FEATURE:
<223> OTHER INFORMATION: Marker probe

<400> SEQUENCE: 5
atatatatat                                                             10
```

<210> SEQ ID NO 6
<211> LENGTH: 43
<212> TYPE: DNA
<213> ORGANISM: Artificial Sequence
<220> FEATURE:
<223> OTHER INFORMATION: Neisseria gonorrhoeae Probing Oligonucleotide 2
      (NG-PO-2)

<400> SEQUENCE: 6
tgcccctcat tggcgtgttt cggacgacgg cttggcttta cga                 43

<210> SEQ ID NO 7
<211> LENGTH: 26
<212> TYPE: DNA
<213> ORGANISM: Artificial Sequence
<220> FEATURE:
<223> OTHER INFORMATION: Neisseria gonorrhoeae Capturing Oligonucleotide
      2 (NG-CO-2)

<400> SEQUENCE: 7 tttttcgta aagccaagcc gtcgtc                                     26

<210> SEQ ID NO 8
<211> LENGTH: 35
<212> TYPE: DNA
<213> ORGANISM: Artificial Sequence
<220> FEATURE:
<223> OTHER INFORMATION: Neisseria gonorrhoeae Probing Oligonucleotide 3
      (NG-PO-3)

<400> SEQUENCE: 8
acgacggctt ggctgcccct cattggcgtg tttcg                          35

<210> SEQ ID NO 9
<211> LENGTH: 23
<212> TYPE: DNA
<213> ORGANISM: Artificial Sequence
<220> FEATURE:
<223> OTHER INFORMATION: Neisseria gonorrhoeae Capturing Oligonucleotide
      3 (NG-CO-3)

<400> SEQUENCE: 9
gccaagccgt cgttttttt ttt                                        23

<210> SEQ ID NO 10
<211> LENGTH: 44
<212> TYPE: DNA
<213> ORGANISM: Artificial Sequence
<220> FEATURE:
<223> OTHER INFORMATION: Neisseria gonorrhoeae Probing Oligonucleotide 4
      (NG-PO-4)

<400> SEQUENCE: 10
tgcccctcat tggcgtgttt cgtgacgacg gcttggcttt acga                44

<210> SEQ ID NO 11
<211> LENGTH: 21
<212> TYPE: DNA
<213> ORGANISM: Artificial Sequence
<220> FEATURE:
<223> OTHER INFORMATION: Neisseria gonorrhoeae forward primer (NG-F)

<400> SEQUENCE: 11
tacgcctgct actttcacgc t                                         21

<210> SEQ ID NO 12
<211> LENGTH: 22

```
<212> TYPE: DNA
<213> ORGANISM: Artificial Sequence
<220> FEATURE:
<223> OTHER INFORMATION: Neisseria gonorrhoeae Probing Oligonucleotide 5
      (NG-PO-5)

<400> SEQUENCE: 12
tgcccctcat tggcgtgttt cg                                              22
```